(12) United States Patent
Huang

(10) Patent No.: US 11,166,826 B2
(45) Date of Patent: Nov. 9, 2021

(54) MULTI-SECTION EXPANDABLE DEVICE

(71) Applicant: OSSAWARE BIOTECH CO., LTD., Changhua County (TW)

(72) Inventor: Max Huang, Changhua County (TW)

(73) Assignee: OSSAWARE BIOTECH CO., LTD., Changhua County (TW)

(*) Notice: Subject to any disclaimer, the term of this patent is extended or adjusted under 35 U.S.C. 154(b) by 166 days.

(21) Appl. No.: 16/681,839

(22) Filed: Nov. 13, 2019

(65) Prior Publication Data

US 2021/0137695 A1   May 13, 2021

(51) Int. Cl.
*A61F 2/44* (2006.01)
*A61F 2/30* (2006.01)

(52) U.S. Cl.
CPC .... *A61F 2/447* (2013.01); *A61F 2002/30158* (2013.01); *A61F 2002/30331* (2013.01); *A61F 2002/30433* (2013.01); *A61F 2002/30579* (2013.01); *A61F 2002/30604* (2013.01); *A61F 2002/30823* (2013.01)

(58) Field of Classification Search
CPC .......... A61F 2/44; A61F 2/442; A61F 2/4455; A61F 2/447
See application file for complete search history.

(56) References Cited

U.S. PATENT DOCUMENTS

| | | | | |
|---|---|---|---|---|
| 8,852,279 B2 * | 10/2014 | Weiman | ................ | A61F 2/4611 623/17.11 |
| 9,233,007 B2 * | 1/2016 | Sungarian | ............... | A61F 2/442 |
| 9,351,848 B2 * | 5/2016 | Glerum | .................... | A61F 2/446 |
| 9,370,433 B1 * | 6/2016 | Morris | ..................... | A61F 2/447 |
| 9,737,411 B2 * | 8/2017 | Loebl | ..................... | A61F 2/4455 |
| 9,795,493 B1 * | 10/2017 | Bannigan | .............. | A61F 2/4455 |
| 9,814,602 B2 * | 11/2017 | Faulhaber | .............. | A61F 2/4611 |
| 9,925,062 B2 * | 3/2018 | Glerum | .................... | A61F 2/442 |
| 10,022,241 B2 * | 7/2018 | Faulhaber | .............. | A61F 2/4611 |
| 10,034,769 B2 * | 7/2018 | Baynham | ................ | A61F 2/447 |
| 10,105,238 B2 * | 10/2018 | Koch | ......................... | A61F 2/44 |
| 10,413,423 B2 * | 9/2019 | Overes | .................. | A61F 2/4611 |
| 10,507,116 B2 * | 12/2019 | Shoshtaev | ............. | A61F 2/4611 |
| 10,617,530 B2 * | 4/2020 | Siegal | .................... | A61F 2/4611 |
| 10,682,239 B2 * | 6/2020 | Hsu | .......................... | A61F 2/447 |
| 10,722,377 B2 * | 7/2020 | Glerum | .................... | A61F 2/447 |
| 10,864,087 B2 * | 12/2020 | Faulhaber | ............... | A61F 2/447 |
| 10,898,340 B2 * | 1/2021 | Koch | ..................... | A61F 2/4455 |

(Continued)

*Primary Examiner* — Eric S Gibson
(74) *Attorney, Agent, or Firm* — Leong C. Lei

(57) ABSTRACT

A multi-section expandable device includes an expansion module, a first push member and a second push member disposed at front and rear ends of the expansion module, and a bolt screwedly connected to the first and second push members. When the bolt is tightened, the first push member and the second push member are pushed to approach each other so as to push the expansion module to generate a first-stage expansion and a second-stage expansion. The first-stage expansion enables the expansion module to expand laterally so as to adjust its width. The second-stage expansion is performed after the expansion module is laterally expanded to have a maximum width, so that the expansion module is longitudinally expanded to adjust its height. The multi-section expandable device not only has better support effect, but also avoids the wear of the contact surfaces of the vertebrae.

15 Claims, 18 Drawing Sheets

(56) References Cited

U.S. PATENT DOCUMENTS

| | | | | |
|---|---|---|---|---|
| 11,033,401 B2* | 6/2021 | Shoshtaev | | A61F 2/447 |
| 2008/0140207 A1* | 6/2008 | Olmos | | A61B 17/025 |
| | | | | 623/17.16 |
| 2010/0286783 A1* | 11/2010 | Lechmann | | A61F 2/44 |
| | | | | 623/17.12 |
| 2012/0310350 A1* | 12/2012 | Farris | | A61F 2/447 |
| | | | | 623/17.16 |
| 2013/0158668 A1* | 6/2013 | Nichols | | A61F 2/4455 |
| | | | | 623/17.16 |
| 2013/0158669 A1* | 6/2013 | Sungarian | | A61F 2/447 |
| | | | | 623/17.16 |
| 2013/0190876 A1* | 7/2013 | Drochner | | A61F 2/442 |
| | | | | 623/17.16 |
| 2014/0039622 A1* | 2/2014 | Glerum | | A61F 2/446 |
| | | | | 623/17.15 |
| 2014/0094916 A1* | 4/2014 | Glerum | | A61F 2/4425 |
| | | | | 623/17.15 |
| 2015/0012098 A1* | 1/2015 | Eastlack | | A61F 2/447 |
| | | | | 623/17.15 |
| 2015/0094813 A1* | 4/2015 | Lechmann | | A61F 2/442 |
| | | | | 623/17.15 |
| 2016/0310290 A1* | 10/2016 | Glerum | | A61F 2/442 |
| 2017/0056200 A1* | 3/2017 | Koch | | A61F 2/4455 |
| 2018/0177605 A1* | 6/2018 | Glerum | | A61F 2/4611 |
| 2018/0193164 A1* | 7/2018 | Shoshtaev | | A61F 2/4425 |
| 2018/0344476 A1* | 12/2018 | Koch | | A61F 2/44 |
| 2019/0117409 A1* | 4/2019 | Shoshtaev | | A61F 2/4611 |
| 2020/0093609 A1* | 3/2020 | Shoshtaev | | A61F 2/447 |
| 2020/0323643 A1* | 10/2020 | Glerum | | A61F 2/4611 |
| 2020/0352731 A1* | 11/2020 | Berry | | A61F 2/447 |
| 2021/0137695 A1* | 5/2021 | Huang | | A61F 2/447 |

* cited by examiner

MULTI-SECTION EXPANDABLE DEVICE

FIELD OF THE INVENTION

The present invention relates to an expandable implant, and more particularly to a multi-section expandable device. Regardless of how large the distance between the upper and lower vertebrae is, the multi-section expandable device can expand to have a larger width, thereby providing a better support effect and avoiding the wear of the contact faces of the vertebrae.

BACKGROUND OF THE INVENTION

At present, the minimally invasive surgery of intervertebral fusion is mainly to create a tiny channel in the affected part, and then an intervertebral infusion device is implanted to be between the upper and lower vertebrae of the affected part using the endoscope or X-ray. The intervertebral infusion device is longitudinally expanded to abut against the opposite end faces of the upper and lower vertebrae for accomplishing the intervertebral fusion.

A conventional intervertebral infusion device, as disclosed in U.S. Pat. Nos. 9,883,955 B2 and 10,045,858 B2, can be expanded in one direction only. When the intervertebral infusion device is longitudinally implanted between the upper and lower vertebrae, it can expand longitudinally to support the upper and lower vertebrae. Since the contact area between the intervertebral infusion device and the upper and lower vertebrae is very small, the end faces of the upper and lower vertebrae are worn easily to cause a depression. When the intervertebral infusion device is laterally implanted between the upper and lower vertebrae, it can expand laterally to increase the width so as to increase the contact area, thereby improving the wear and depression of the vertebrae. However, the height is immovable and cannot be adjusted. Therefore, once the distance between the upper and lower vertebrae of the patient is large, the intervertebral infusion device is unable to abut against the opposite end faces of the upper and lower vertebrae, failing to accomplish the intervertebral fusion.

Another conventional intervertebral infusion device, as disclosed in U.S. Pat. Nos. 8,864,833 B2 and 10,098,758 B2, can be expanded longitudinally and transversely. However, because the size of the human body, the severity of the disease and the affected part are different, the required height of the longitudinal expansion of the intervertebral infusion device will be different. Therefore, when the intervertebral infusion device is implanted between the upper and lower vertebrae that need a large longitudinal expansion, it can be expanded longitudinally and laterally to the maximum, not having the problem that the end faces of the upper and lower vertebrae are worn easily to cause a depression. However, when the intervertebral infusion device is implanted between the upper and lower vertebrae that need a small longitudinal expansion, the distance of the longitudinal expansion is limited and only small or even no. The lateral expansion is linked with the longitudinal expansion, so the distance of the lateral expansion will be relatively small or even no. There is still a problem that the end faces of the upper and lower vertebrae are worn easily to cause a depression because the width is not enough. Furthermore, the longitudinal expansion and the lateral expansion are performed at the same time to cause a relatively large operational resistance, and thus there are problems such as poor smoothness and laboriousness.

SUMMARY OF THE INVENTION

The primary object of the present invention is to provide a multi-section expandable device, comprising an expansion module, a first push member, a second push member, and a bolt. The expansion module is able to expand longitudinally and laterally. The first push member is disposed at a front end of the expansion module and has a screw hole therein. The second push member is disposed at a rear end of the expansion module and has a through hole therein. The bolt has a screw portion and a head portion with a larger outer diameter. The screw portion is inserted through the through hole of the second push member and screwed in the screw hole of the first push member. The head portion abuts against one side of the second push member opposite to the first push member. When the bolt is tightened, the first push member and the second push member are pushed to approach each other so as to push the expansion module to generate a first-stage expansion and a second-stage expansion. The first-stage expansion enables the expansion module to expand laterally so as to adjust its width. The second-stage expansion is performed after the expansion module is laterally expanded to have a maximum width, so that the expansion module is longitudinally expanded to adjust its height.

The multi-section expandable device provided by the present invention firstly performs the first-stage expansion for the expansion module to expand laterally to have the maximum width, and then performs the second-stage expansion for the expansion module to expand longitudinally to adjust its height. Therefore, no matter how much height is required between the upper and lower vertebrae, the expansion module can be expanded laterally to have the maximum width and a large contact area. It not only has better support effect, but also avoids the wear of the contact surfaces of the vertebrae. The multi-section expandable device with a single specification can be applied to the intervertebral disc space of various body sizes, different diseases and different affected parts. Moreover, the two-stage expansion can greatly reduce the operational resistance, thereby increasing the smoothness and being labor-saving.

DETAILED DESCRIPTION OF THE PREFERRED EMBODIMENTS

Figure 1:
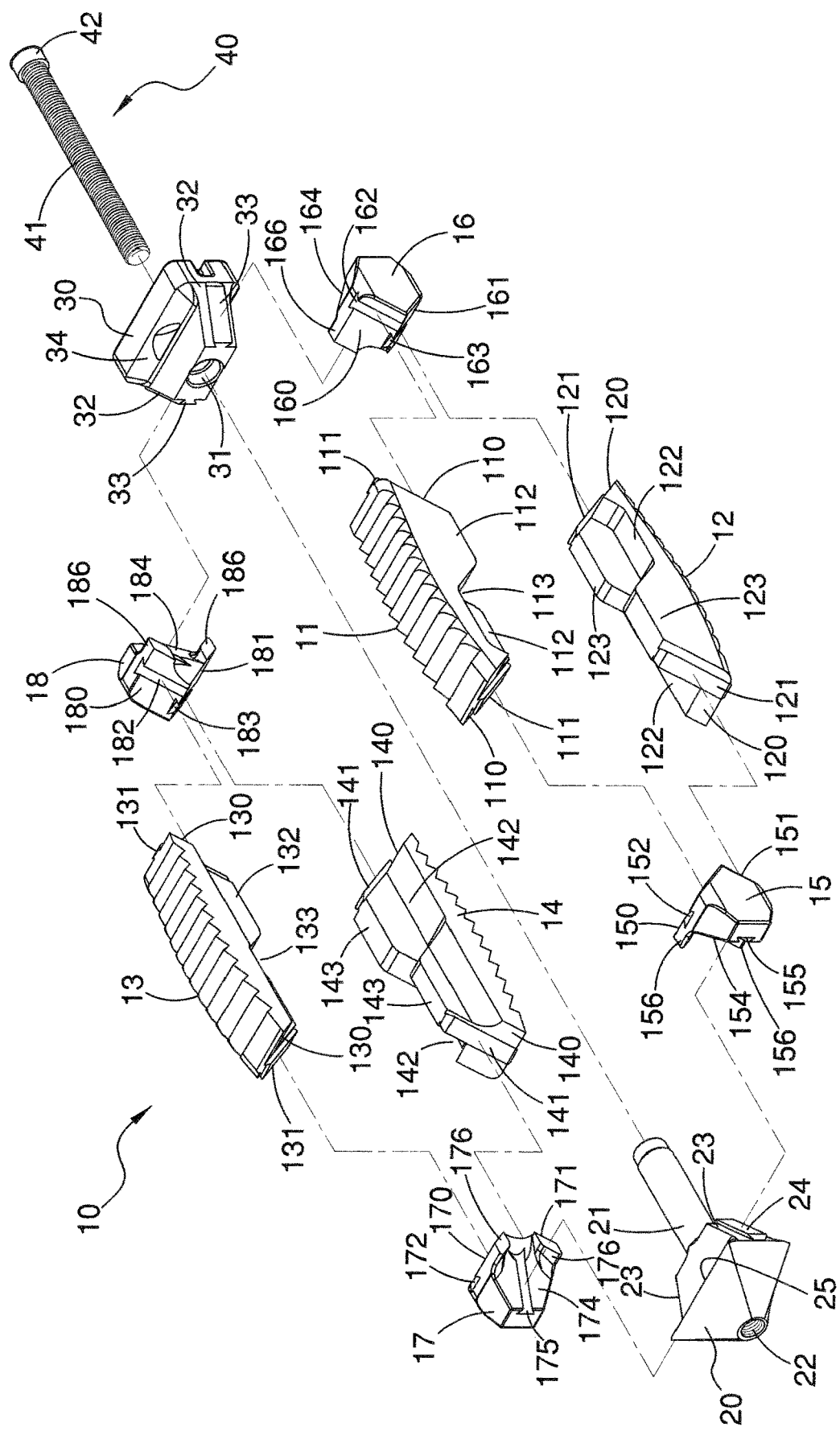
FIG. 1 is an exploded view in accordance with a first embodiment of the present invention.
Figure 2:
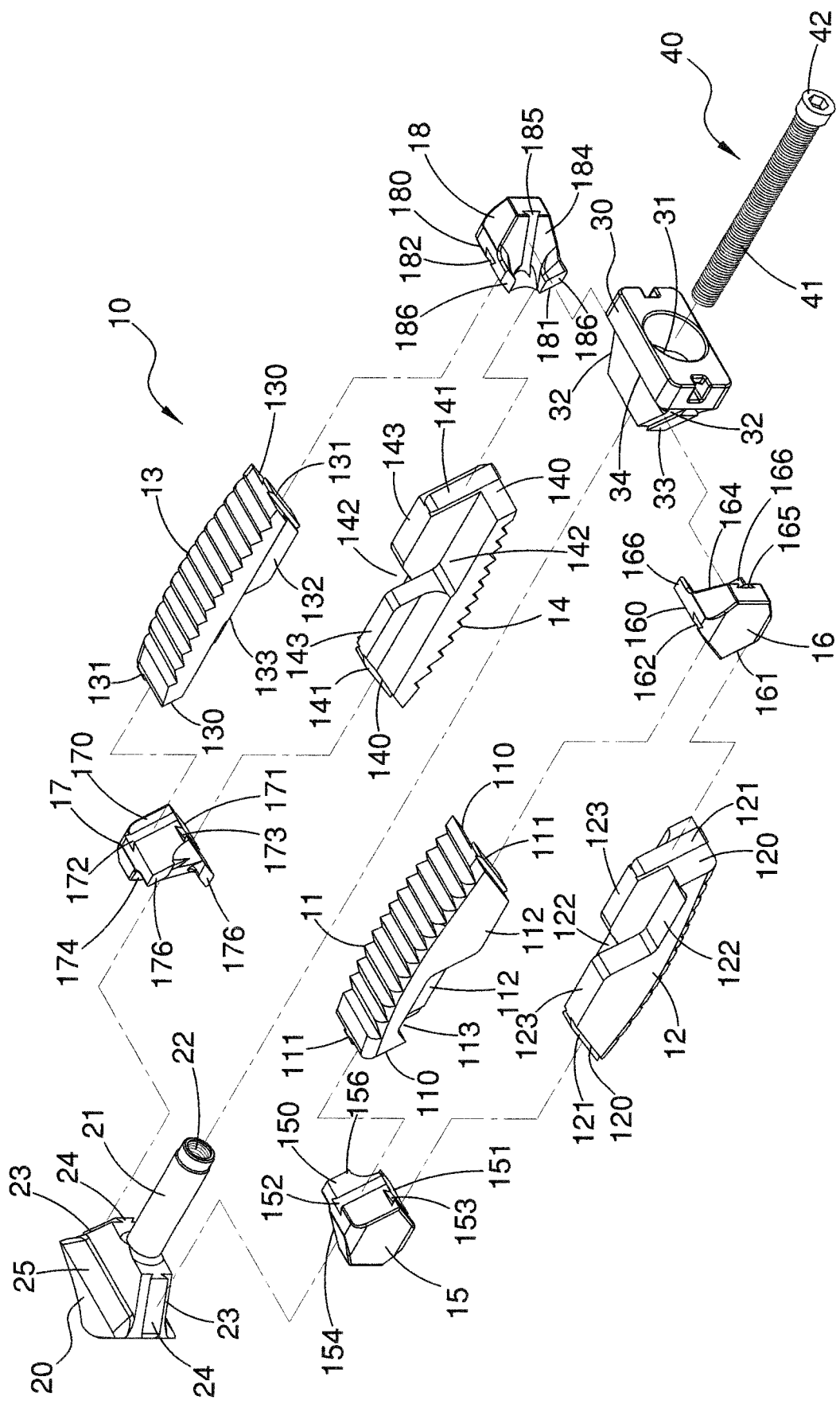
FIG. 2 is another exploded view in accordance with the first embodiment of the present invention.

Embodiments of the present invention will now be described, by way of example only, with reference to the accompanying drawings.

FIGS. 1-14 illustrate a two-stage expandable intervertebral fusion device in accordance with a first embodiment of the present invention.

As shown in FIGS. 1-8, the multi-section expandable device of the present invention comprises an expansion module 10, a first push member 20, a second push member 30, and a bolt 40.

The expansion module 10 is able to expand longitudinally and laterally.

The first push member 20 is disposed at a front end of the expansion module 10. A rod 21 is protruded from a rear side of the first push member 20. The rod 21 has a screw hole 22 therein.

The second push member 30 is disposed at a rear end of the expansion module 10. The second push member 30 has a through hole 31 therein.

The bolt 40 has a screw portion 41 and a head portion 42 with a larger outer diameter. The screw portion 41 is inserted through the through hole 31 of the second push member 30 and screwed in the screw hole 22 of the first push member 20. The head portion 42 abuts against one side of the second push member 30 opposite to the first push member 20.

Figure 3:
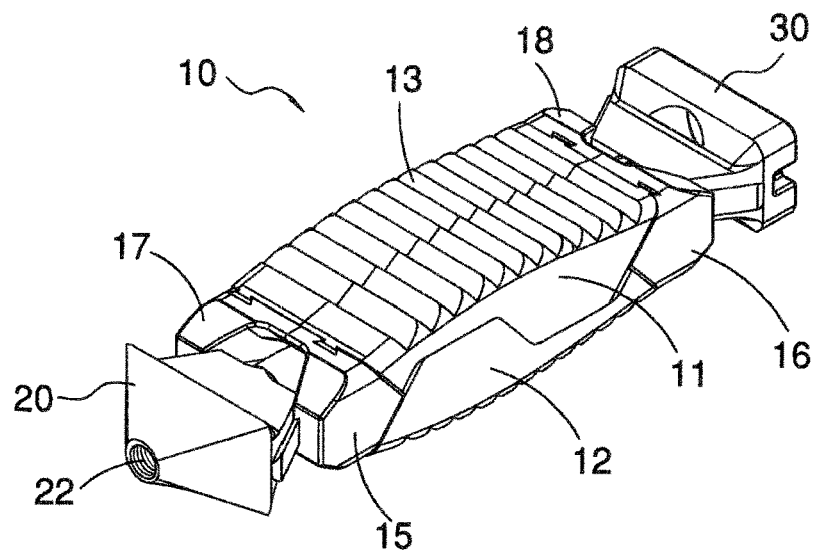
FIG. 3 is a perspective view in accordance with the first embodiment of the present invention.
Figure 4:
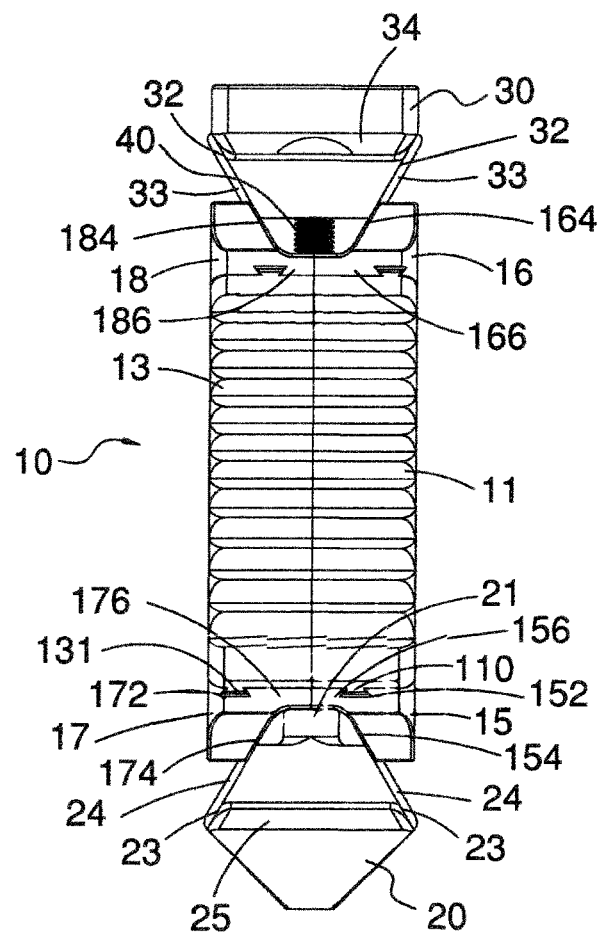
FIG. 4 is a top view of FIG. 3.
Figure 5:
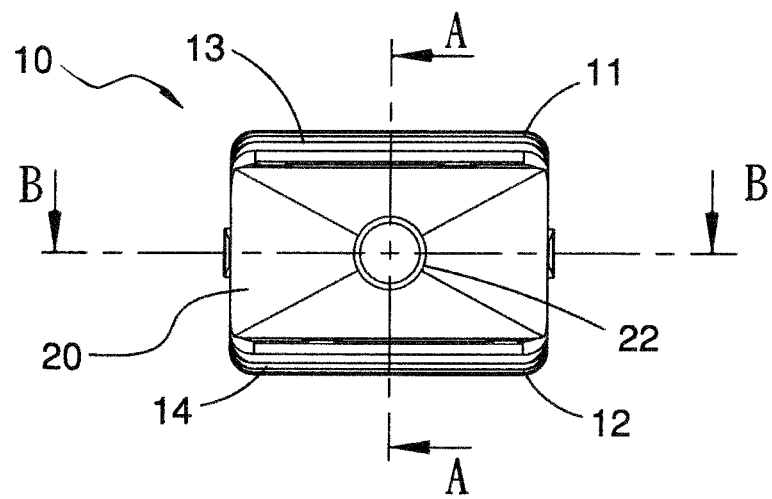
FIG. 5 is a front view of FIG. 3.
Figure 6:
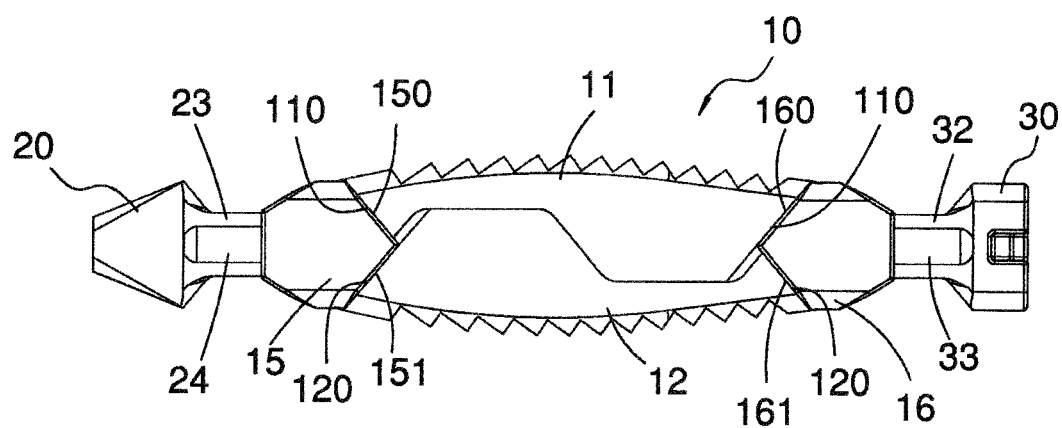
FIG. 6 is a right side view of FIG. 3.
Figure 7:
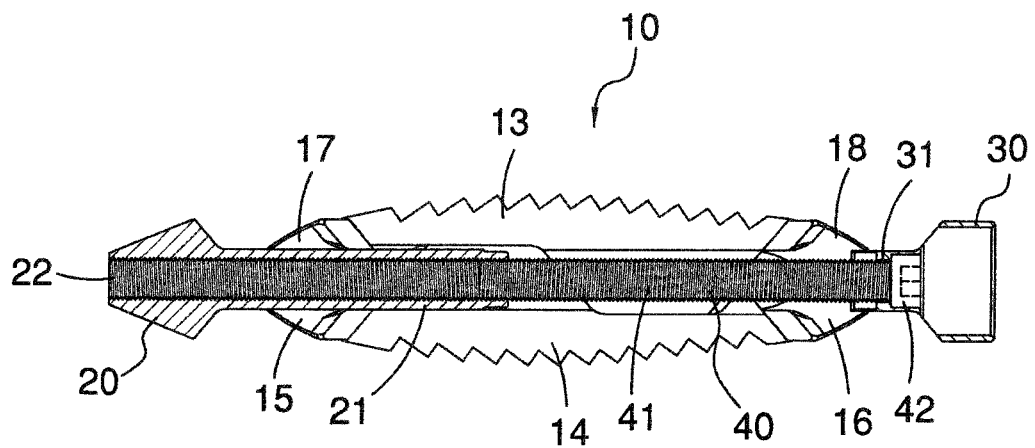
FIG. 7 is a cross-sectional view taken along line A-A of FIG. 5.
Figure 8:
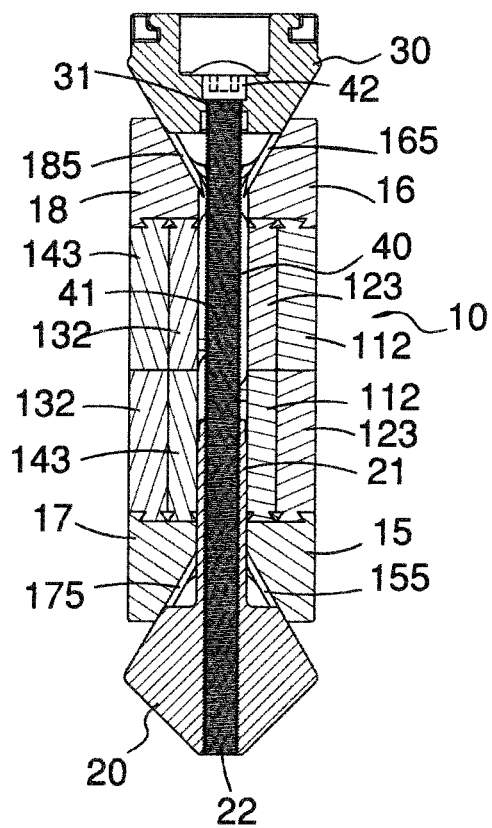
FIG. 8 is a cross-sectional view taken along line B-B of FIG. 5.
Figure 9:
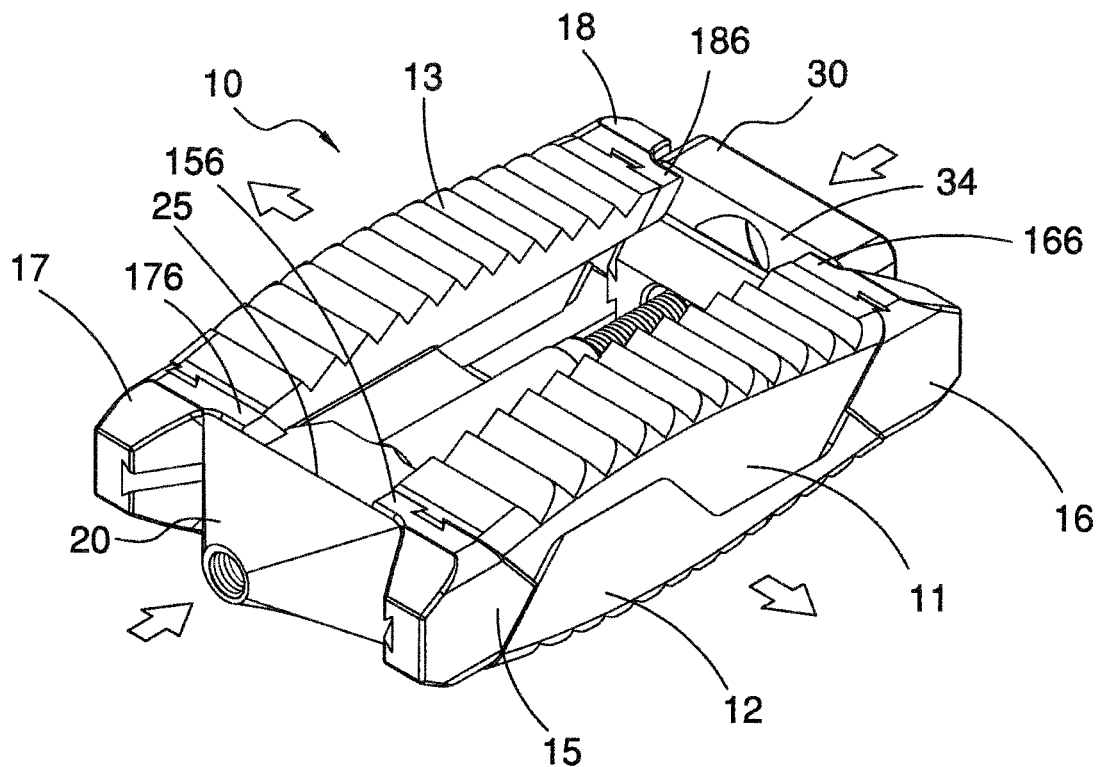
FIG. 9 is a perspective view showing the first-stage expansion in accordance with the first embodiment of the present invention.
Figure 12:
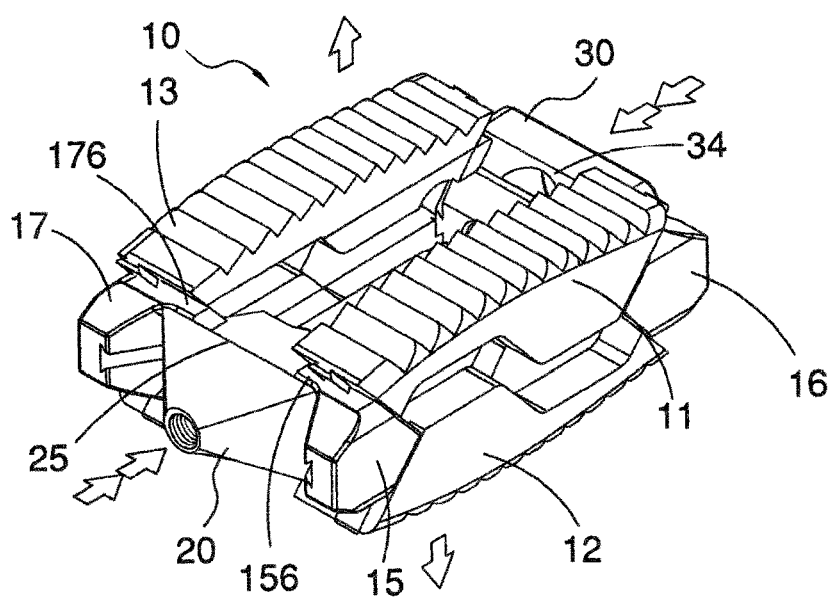
FIG. 12 is a perspective view showing the second-stage expansion in accordance with the first embodiment of the present invention.

Referring to the FIG. 3, FIG. 9 and FIG. 12, when the bolt 40 is tightened, the first push member 20 and the second push member 30 are pushed to approach each other so as to push the expansion module 10 to generate a first-stage expansion and a second-stage expansion, the first-stage expansion enables the expansion module 10 to expand laterally to adjust its width, the second-stage expansion is performed after the expansion module 10 is laterally expanded to have a maximum width, so that the expansion module 10 can be longitudinally expanded to adjust its height as needed.

The expansion module 10 includes a first expansion block 11, a second expansion block 12, a third expansion block 13, a fourth expansion block 14, a first guide block 15, a second guide block 16, a third guide block 17, and a fourth guide block 18.

The first expansion block 11 has a toothed top surface. Front and rear ends of the first expansion block 11 are formed with two first inclined planes 110 that are inclined outwardly from bottom to top, respectively. Two first inclined plane guide rails 111 are disposed on the two first inclined planes 110, respectively. A bottom surface of the first expansion block 11 has a plurality of first guide protrusions 112 and a plurality of first guide grooves 113 which are staggered and each have a trapezoidal shape.

The second expansion block 12 is located under the first expansion block 11 and has a toothed button surface. Front and rear ends of the second expansion block 12 are formed with two second inclined planes 120 that are inclined outwardly from top to bottom, respectively. Two second inclined plane guide rails 121 are disposed on the two second inclined planes 120, respectively. A top surface of the second expansion block 12 has a plurality of second guide grooves 122 and a plurality of second guide protrusions 123 which can be slid up and down relative to the plurality of first guide protrusions 112 and the plurality of first guide grooves 113.

The third expansion block 13 is located beside the first expansion block 11 has a toothed top surface. Front and rear ends of the third expansion block 13 are formed with two third inclined planes 130 that are inclined outwardly from bottom to top, respectively. Two second inclined plane guide rails 113 are disposed on the two second inclined planes 130, respectively. A bottom surface of the third expansion block 13 has a plurality of third guide protrusions 132 and a plurality of third guide grooves 133 which are staggered and each have a trapezoidal shape.

The fourth expansion block 14 is located under the third expansion block 13 and has a toothed button surface. Front and rear ends of the fourth expansion block 14 are formed with two fourth inclined planes 140 that are inclined outwardly from top to bottom, respectively. Two fourth inclined plane guide rails 141 are disposed on the two fourth inclined planes 140, respectively. A top surface of the fourth expansion block 14 has a plurality of fourth guide grooves 142 and a plurality of fourth guide protrusions 143 which can be slid up and down relative to the plurality of third guide protrusions 132 and the plurality of third guide grooves 133.

The first guide block 15 is disposed on the front end faces of the first and second expansion blocks 11, 12. A rear end of the first guide block 15 is formed with a first upper inclined plane 150 and a first lower inclined plane 151 corresponding to the first and second inclined planes 110, 120 on the front ends of the first and second expansion blocks 11, 12. The first upper inclined plane 150 is provided with a first upper dovetailed groove 152 for the first inclined plane guide rail 111 on the front end of the first expansion block 11 to be inserted therein. The first lower inclined plane 151 is provided with a first lower dovetailed groove 153 for the second inclined plane guide rail 121 on the front end of the second expansion block 12 to be inserted therein. A front end of the first guide block 15 is formed with a first front inclined plane 154 that is inclined outwardly from back to front. The first front inclined plane 154 is provided with a first front dovetailed groove 155. Two first front stop pieces 156 are protruded from a lower end of the first front inclined plane 154.

The second guide block 16 is disposed on the rear end faces of the first and second expansion blocks 11, 12. A front end of the second guide block 16 is formed with a second upper inclined plane 160 and a second lower inclined plane 161 corresponding to the first and second inclined planes 110, 120 on the rear ends of the first and second expansion blocks 11, 12. The second upper inclined plane 160 is provided with a second upper dovetailed groove 162 for the first inclined plane guide rail 111 on the rear end of the first expansion block 11 to be inserted therein. The second lower inclined plane 161 is provided with a second lower dovetailed groove 163 for the second inclined plane guide rail 121 on the rear end of the second expansion block 12 to be inserted therein. A rear end of the second guide block 16 is formed with a second rear inclined plane 164 that is inclined outwardly from front to back. The second rear inclined plane 164 is provided with a second rear dovetailed groove 165. Two second rear stop pieces 166 are protruded from a lower end of the second rear inclined plane 164.

The third guide block 17 is disposed on the front end faces of the third and fourth expansion blocks 13, 14. A rear end of the third guide block 17 is formed with a third upper inclined plane 170 and a third lower inclined plane 171 corresponding to the third and fourth inclined planes 130, 140 on the front ends of the third and fourth expansion blocks 13, 14. The third upper inclined plane 170 is provided with a third upper dovetailed groove 172 for the third inclined plane guide rail 131 on the front end of the third expansion block 13 to be inserted therein. The third lower inclined plane 171 is provided with a third lower dovetailed groove 173 for the fourth inclined plane guide rail 141 on the front end of the fourth expansion block 14 to be inserted therein. A front end of the third guide block 17 is formed with a third front inclined plane 174 that is inclined outwardly from back to front. The third front inclined plane 174 is provided with a third front dovetailed groove 175. Two third front stop pieces 176 are protruded from a lower end of the third front inclined plane 174.

The fourth guide block 18 is disposed on the rear end faces of the third and fourth expansion blocks 13, 14. A front end of the fourth guide block 18 is formed with a fourth upper inclined plane 180 and a fourth lower inclined plane 181 corresponding to the third and fourth inclined planes 130, 140 on the rear ends of the third and fourth expansion blocks 13, 14. The fourth upper inclined plane 180 is provided with a fourth upper dovetailed groove 182 for the third inclined plane guide rail 131 on the rear end of the third expansion block 13 to be inserted therein. The fourth lower inclined plane 181 is provided with a fourth lower dovetailed groove 183 for the fourth inclined plane guide rail 141 on the rear end of the fourth expansion block 14 to be inserted therein. A rear end of the fourth guide block 18 is formed with a fourth rear inclined plane 184 that is inclined outwardly from front to back. The fourth front inclined plane 184 is provided with a fourth rear dovetailed groove 185. Two fourth rear stop pieces 186 are protruded from a lower end of the fourth rear inclined plane 184.

Two sides of the first push member 20 have two first push member inclined planes 23 corresponding to the first and third front inclined planes 154, 174. The two first push member inclined planes 23 are provided with two first push member guide rails 24 to be inserted in the first and third front dovetailed grooves 155, 175. The first push member 20 has two first stop faces 25 on upper and lower sides thereof.

Two sides of the second push member 30 have two second push member inclined planes 32 corresponding to the second and fourth rear inclined planes 164, 184. The two second push member inclined planes 32 are provided with two second push member guide rails 33 to be inserted in the second and fourth rear dovetailed grooves 165, 185. The second push member 30 has two second stop faces 34 on upper and lower sides thereof.

Figure 10:
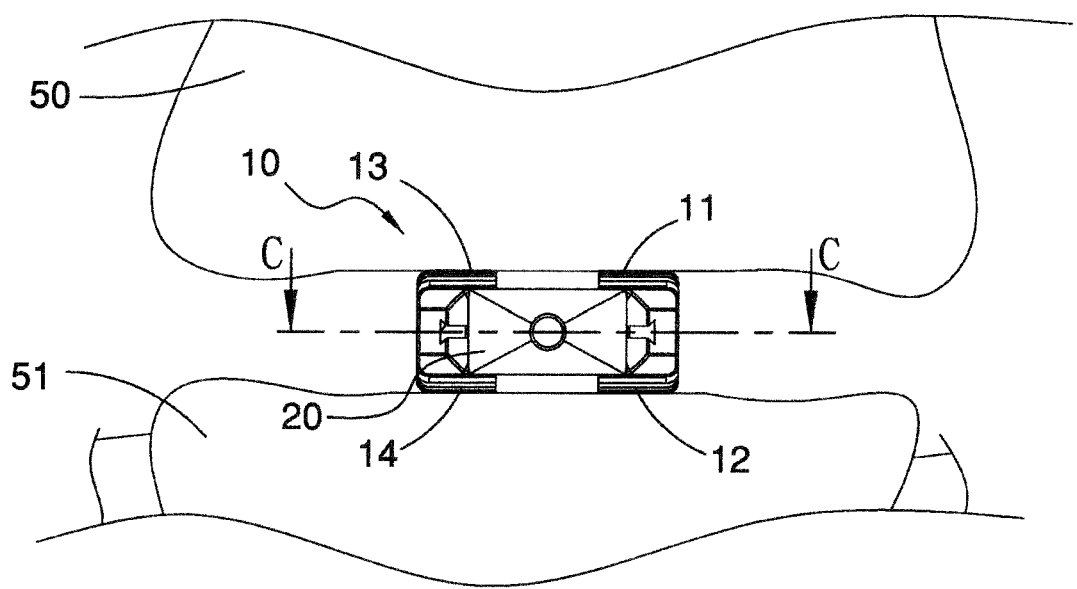
FIG. 10 is front schematic view showing the first-stage expansion in accordance with the first embodiment of the present invention.
Figure 11:
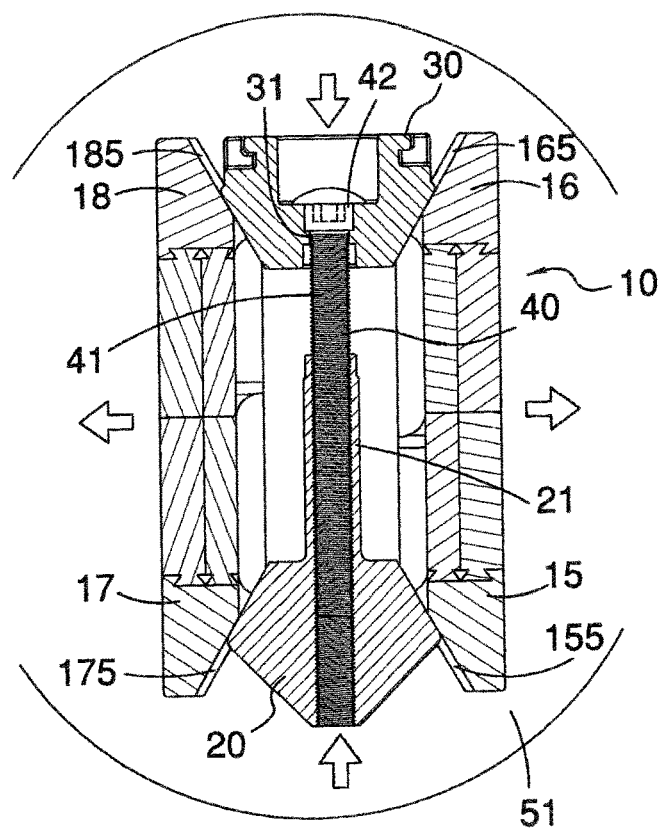
FIG. 11 is an enlarged cross-sectional view taken along line C-C of FIG. 10.

FIGS. 9-11 illustrate the operation for the first-stage expansion of the multi-section expandable device of the present invention. When the bolt 40 is tightened, the first and second push members 20, 30 are pushed to approach each other to synchronously push the first guide block 15, the second guide block 16, the third guide block 17, and the fourth guide block 18. The first and second guide blocks 15, 16 and the third and fourth guide blocks 17, 18 are moved outwardly (left and right) along the two first push member inclined planes 23 of the first push member 20 and the two second push member inclined planes 32 of the second push member 30, respectively, so that the first and second guide blocks 15, 16 and the third and fourth guide blocks 17, 18 respectively drive the first and second expansion blocks 11, 12 and the third and fourth expansion blocks 13, 14 to expand laterally between the first and second push members 20, 30 so as to increase the width of the expansion module 10.

Figure 13:
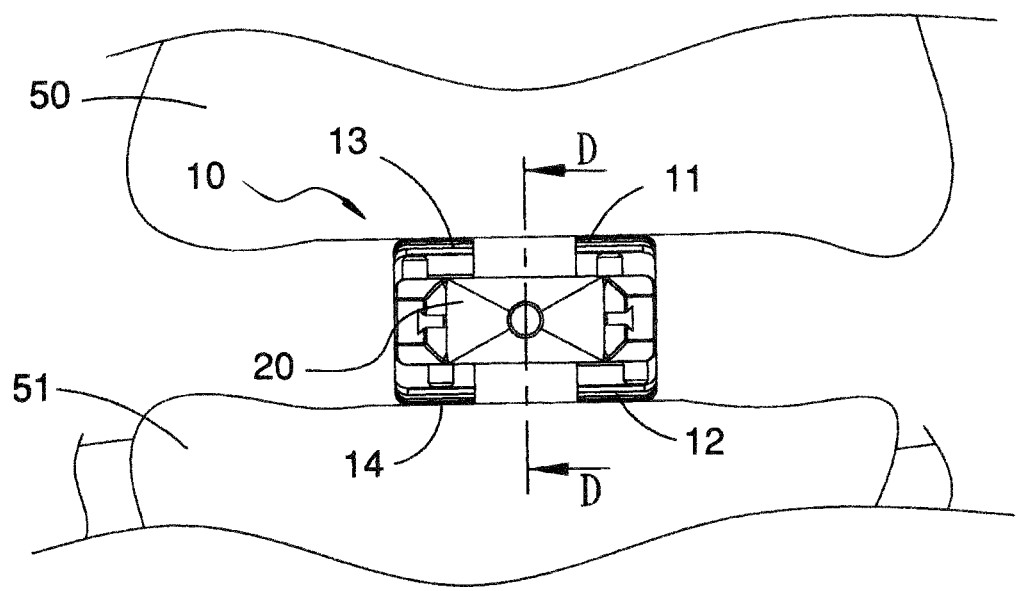
FIG. 13 is front schematic view showing the second-stage expansion in accordance with the first embodiment of the present invention.
Figure 14:
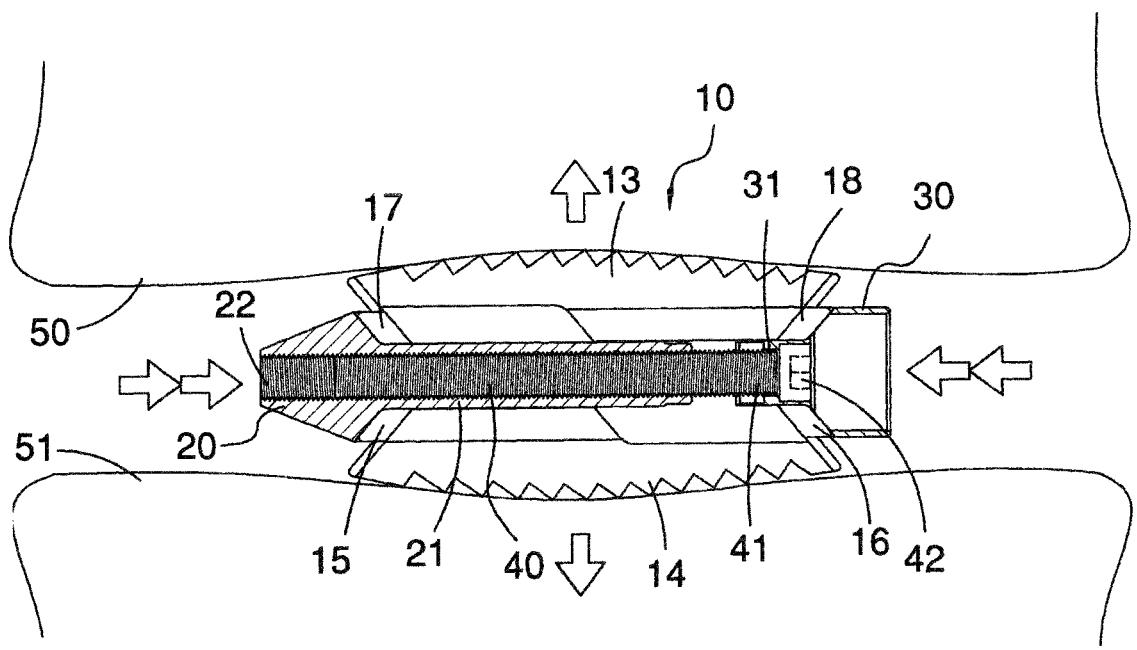
FIG. 14 is an enlarged cross-sectional view taken along line D-D of FIG. 13.
Figure 15:
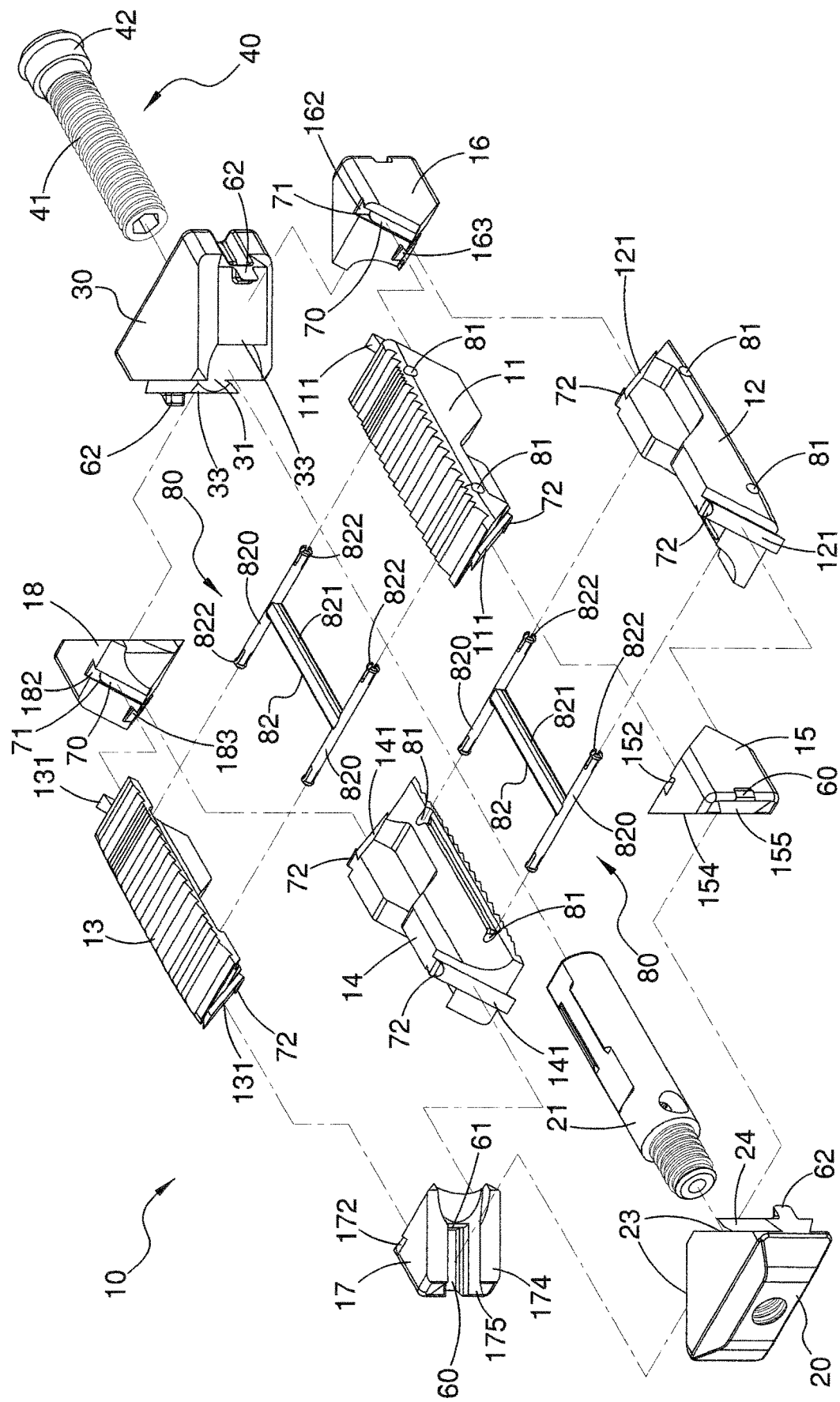
FIG. 15 is an exploded view in accordance with a second embodiment of the present invention.
Figure 16:
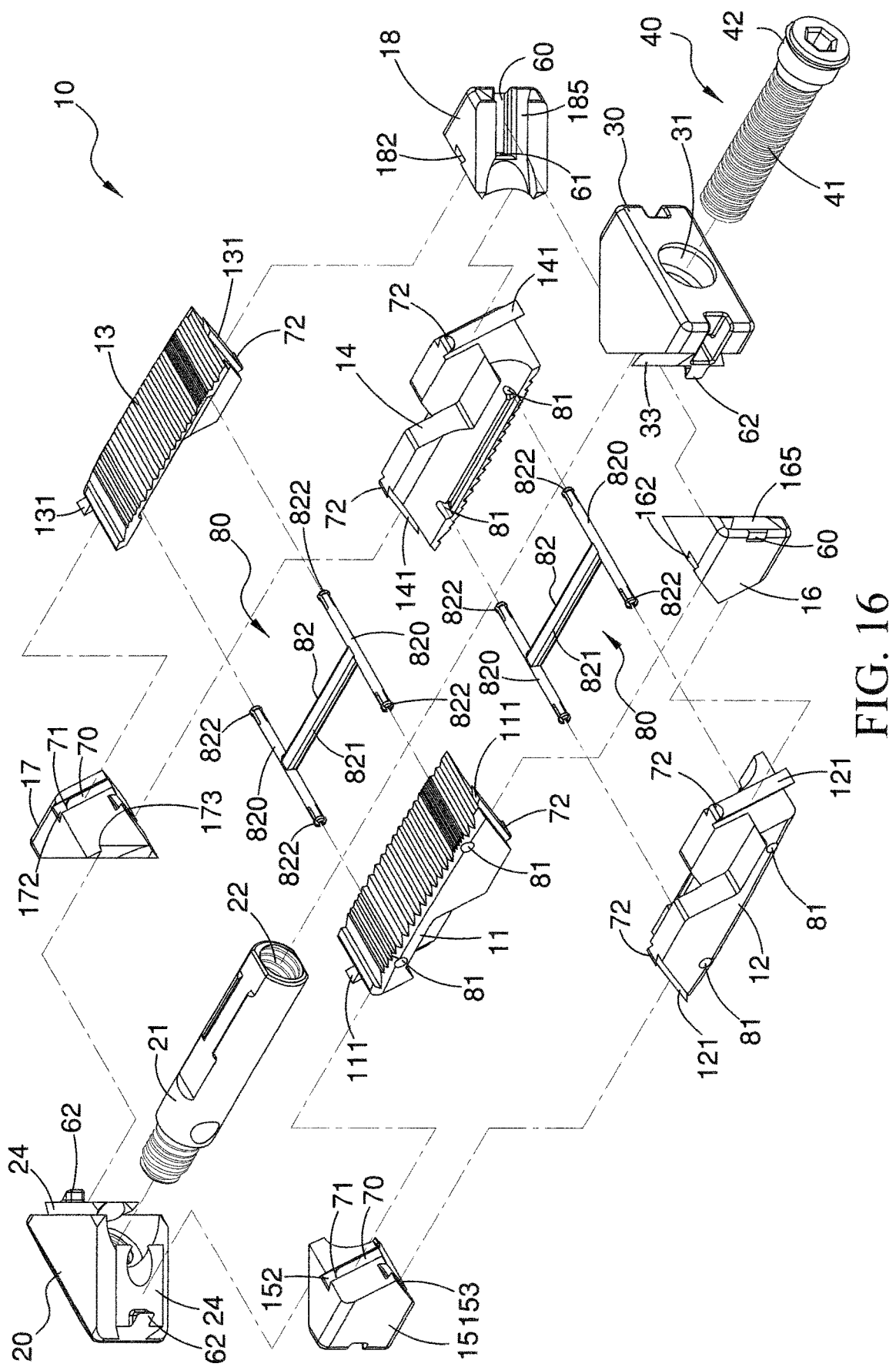
FIG. 16 is another exploded view in accordance with the second embodiment of the present invention.
Figure 17:
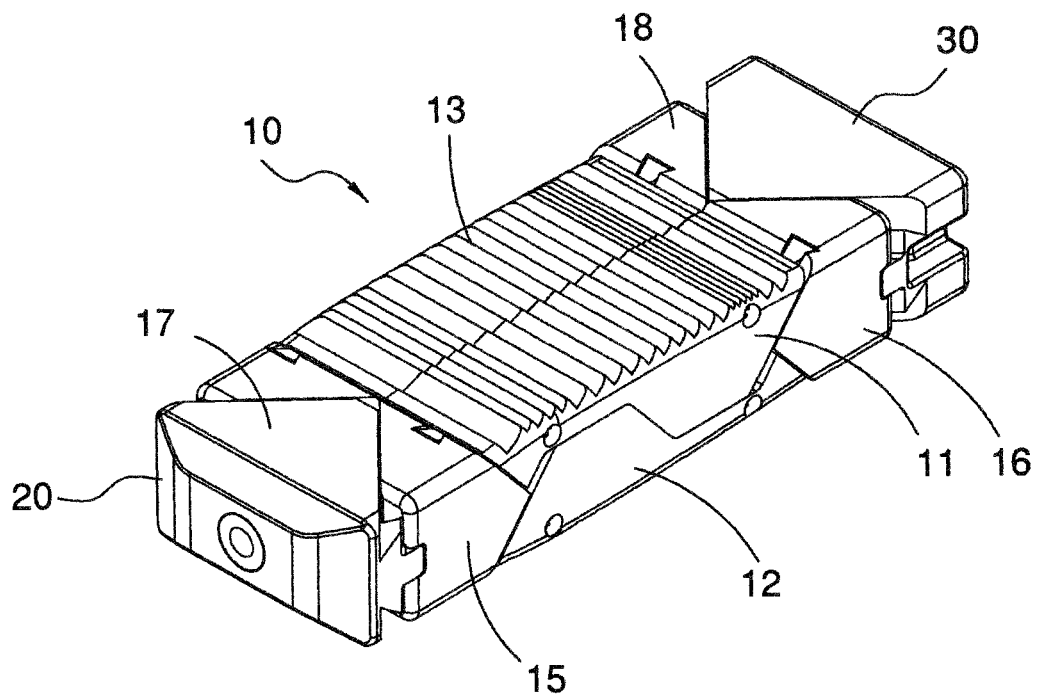
FIG. 17 is a perspective view in accordance with the second embodiment of the present invention in a fully retracted state.

FIGS. 12-14 illustrate the operation for the second-stage expansion of the multi-section expandable device of the present invention. When the two first stop faces 25 and the two second stop faces 34 are blocked by the two first front stop pieces 156, the two third front stop pieces 176 and the two second rear stop pieces 166, the two four rear stop pieces 186 respectively, the first and second expansion blocks 11, 12 and the third and fourth expansion blocks 13, 14 between the first and second push members 20, 30 can no longer continue to expand laterally. At this time, the expansion module 10 is laterally expanded to have the maximum width (this is, the ultimate width of the first-stage expansion). Then, the bolt 40 is further tightened, and the first and second expansion blocks 11, 12 are moved along the first upper inclined plane 150 and the first lower inclined plane 151 of the first guide block 15 and the second upper inclined plane 160 and the second lower inclined plane 161 of the second guide block 16 to expand longitudinally. At the same time, the third and fourth expansion blocks 13, 14 are also moved along the third upper inclined plane 170 and the third lower inclined plane 171 of the third guide block 17 and the fourth upper inclined plane 180 and the fourth lower inclined plane 181 of the fourth guide block 18 to expand longitudinally. Thus, the height of the expansion module 10 can be adjusted to lean against the upper vertebra 50 and the lower vertebra 51.

The multi-section expandable device provided by the present invention firstly performs the first-stage expansion for the expansion module to expand laterally to have the maximum width, and then performs the second-stage expansion for the expansion module to expand longitudinally to adjust its height. Therefore, no matter how much height is required between the upper and lower vertebrae, the expansion module can be expanded laterally to have the maximum width and a larger contact area. It not only has better support effect, but also avoids the wear of the contact surfaces of the vertebrae. The multi-section expandable device with a single specification can be applied to the intervertebral disc space of various body sizes, different diseases and different affected parts. Moreover, the two-stage expansion can greatly reduce the operational resistance, thereby increasing the smoothness and being labor-saving.

FIGS. 15-22 illustrate a second embodiment of the multi-section expandable device of the present invention. The second embodiment is substantially similar to the first embodiment with the exceptions described hereinafter.

(1) In the second embodiment, one end of the rod 21 is coupled to the first push member 20 in a screwed manner.

Figure 18:
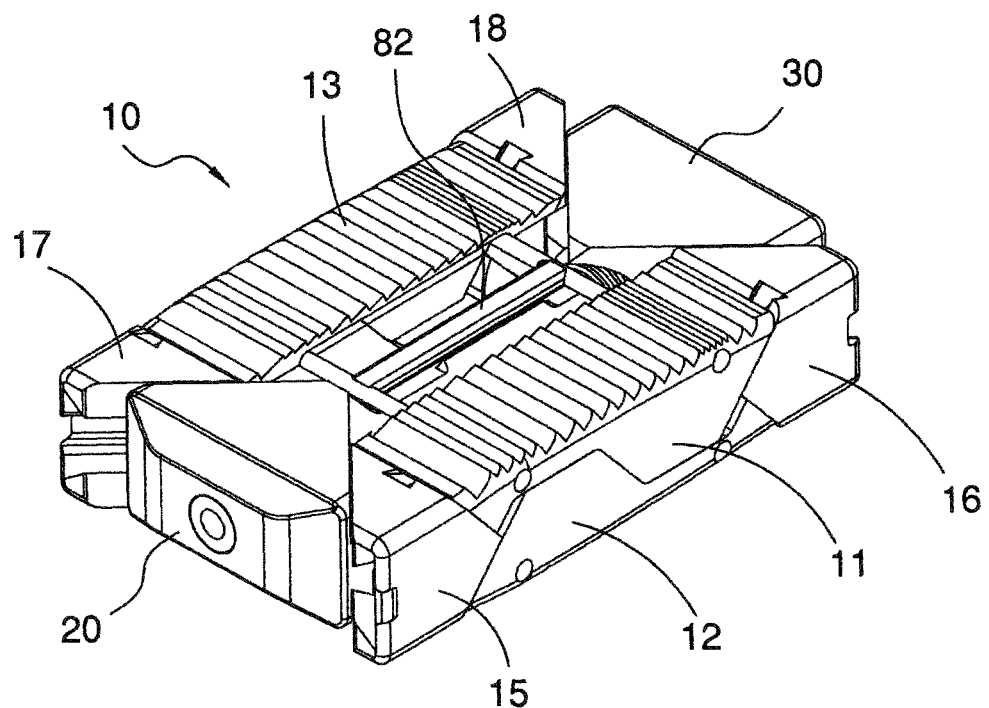
FIG. 18 is a perspective view showing the first-stage expansion to the ultimate in accordance with the second embodiment of the present invention.
Figure 19:
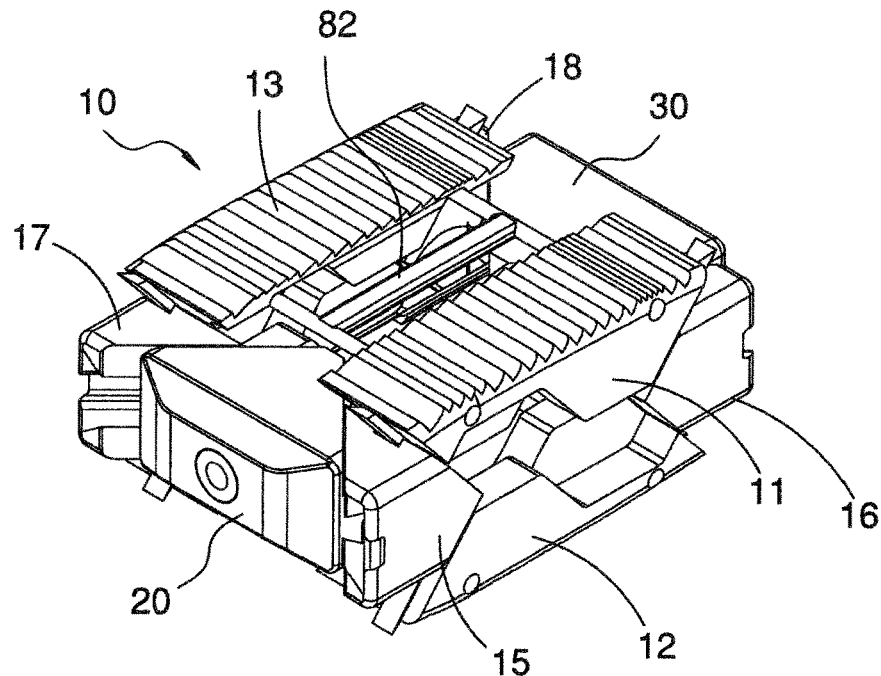
FIG. 19 is a perspective view in accordance with the second embodiment of the present invention in a fully expanded state.
Figure 20:
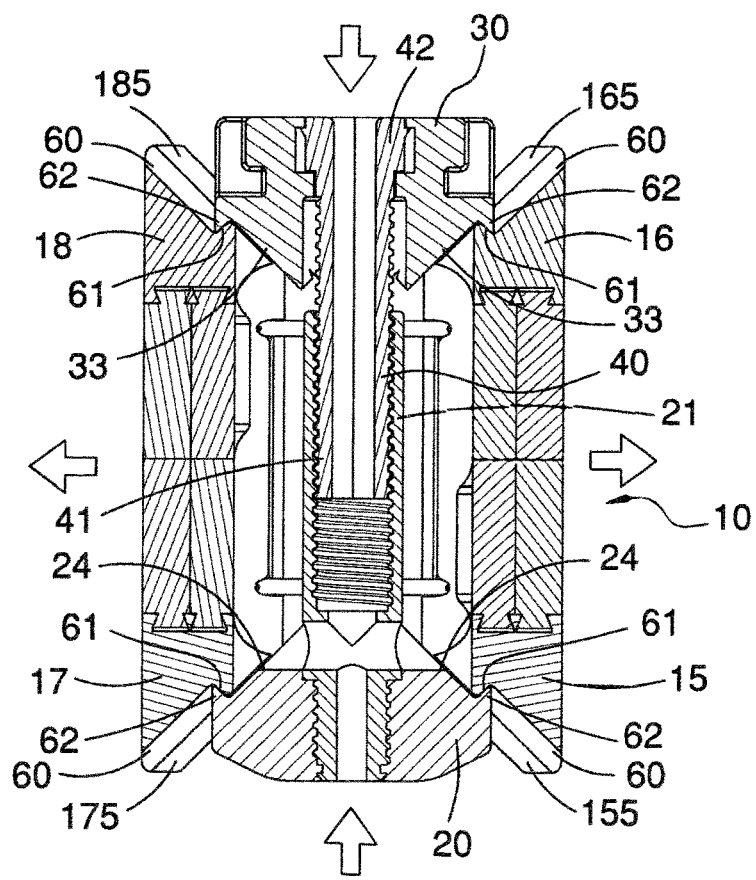
FIG. 20 is a cross-sectional view showing the first-stage expansion to the ultimate in accordance with the second embodiment of the present invention.

(2) In the first embodiment, the two first stop faces 25 and the two second stop faces 34 are respectively blocked by the two first front stop pieces 156, the two third front stop pieces 176 and the two fourth rear stop pieces 166, the two fourth rear stop pieces 86 as the extremity of the first-stage expansion, thus forming a condition for performing the second-stage expansion. In the second embodiment, each of the first front dovetailed groove 155, the second rear dovetailed groove 165, the third front dovetailed groove 175 and the fourth rear dovetailed groove 185 has an ultimate guide groove 60 on a bottom thereof. One end of the ultimate guide groove 60 is an open end, and another end of the ultimate guide groove 60 is formed with an ultimate stop face 61. One end of each of the two first push member guide rails 24 and the two second push member guide rails 33 is provided with a raised portion 62 to be inserted in the ultimate guide groove 60. Referring to FIG. 18 and FIG. 20, when the bolt 40 is tightened until the four raised portions 62 are respectively blocked by the ultimate stop faces 61 of the four ultimate guide grooves 60, the first and second expansion blocks 11, 12 and the third and fourth expansion blocks 13, 14 between the first and second push members 20, 30 cannot continue to expand laterally. At this time, the expansion module 10 is laterally expanded to have the maximum width (this is, the ultimate width of the first-stage expansion). Then, the bolt 40 is further tightened, and the first and second expansion blocks 11, 12 are moved along the first upper inclined plane 150 and the first lower inclined plane 151 of the first guide block 15 and the second upper inclined plane 160 and the second lower inclined plane 161 of the second guide block 16 to expand longitudinally. At the same time, the third and fourth expansion blocks 13, 14 are also moved along the third upper inclined plane 170 and the third lower inclined plane 171 of the third guide block 17 and the fourth upper inclined plane 180 and the fourth lower inclined plane 181 of the fourth guide block 18 to expand longitudinally.

Figure 21:
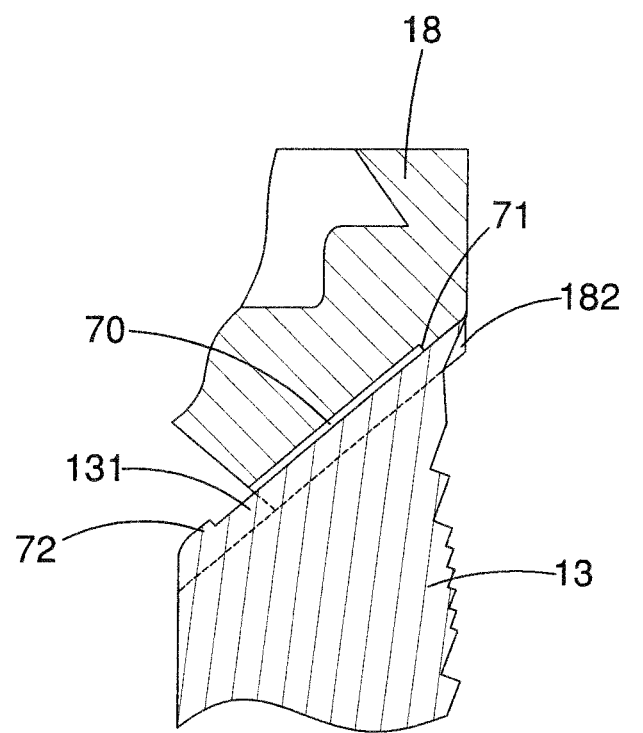
FIG. 21 is a schematic view showing the operation of the limit structure in accordance with the second embodiment of the present invention.
Figure 21:
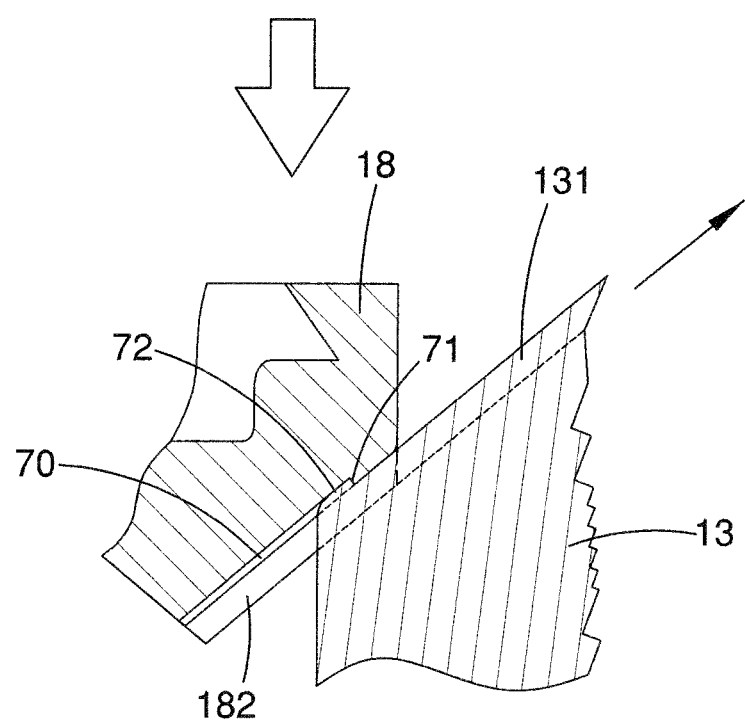

(3) In the second embodiment, each of the first upper dovetailed groove 152, the first lower dovetailed groove 153, the second upper dovetailed groove 162, the second lower dovetailed groove 163, the third upper dovetailed groove 172, the third lower dovetailed groove 173, the fourth upper dovetailed groove 182 and the fourth lower dovetailed groove 183 is provided with a limit guide groove 170 on a bottom thereof. One end of the limit guide groove 70 is an open end, and another end of the limit guide groove 70 is formed with an engaging face 71. One end of each of the two first inclined plane guide rails 111, the two second inclined plane guide rails 121, the two third inclined plane guide rails 131 and the two fourth inclined plane guide rails 141 is provided with an engaging portion 72 to be inserted in the limit guide groove 70. The eight engaging portions 72 are blocked by the engaging faces 71 of the eight limit guide grooves 70 to prevent the first, second, third and fourth expansion blocks 11, 12, 13, 14 from being disengaged from the first, second, third and fourth guide blocks 15, 16, 17, 18 when they are expanded longitudinally. (FIG. 21 illustrates the limit operation of the third inclined plane guide rail 131 and the fourth upper dovetailed groove 182, and the other relative positions are the same. Therefore, it is no longer shown in the figures).

Figure 22:
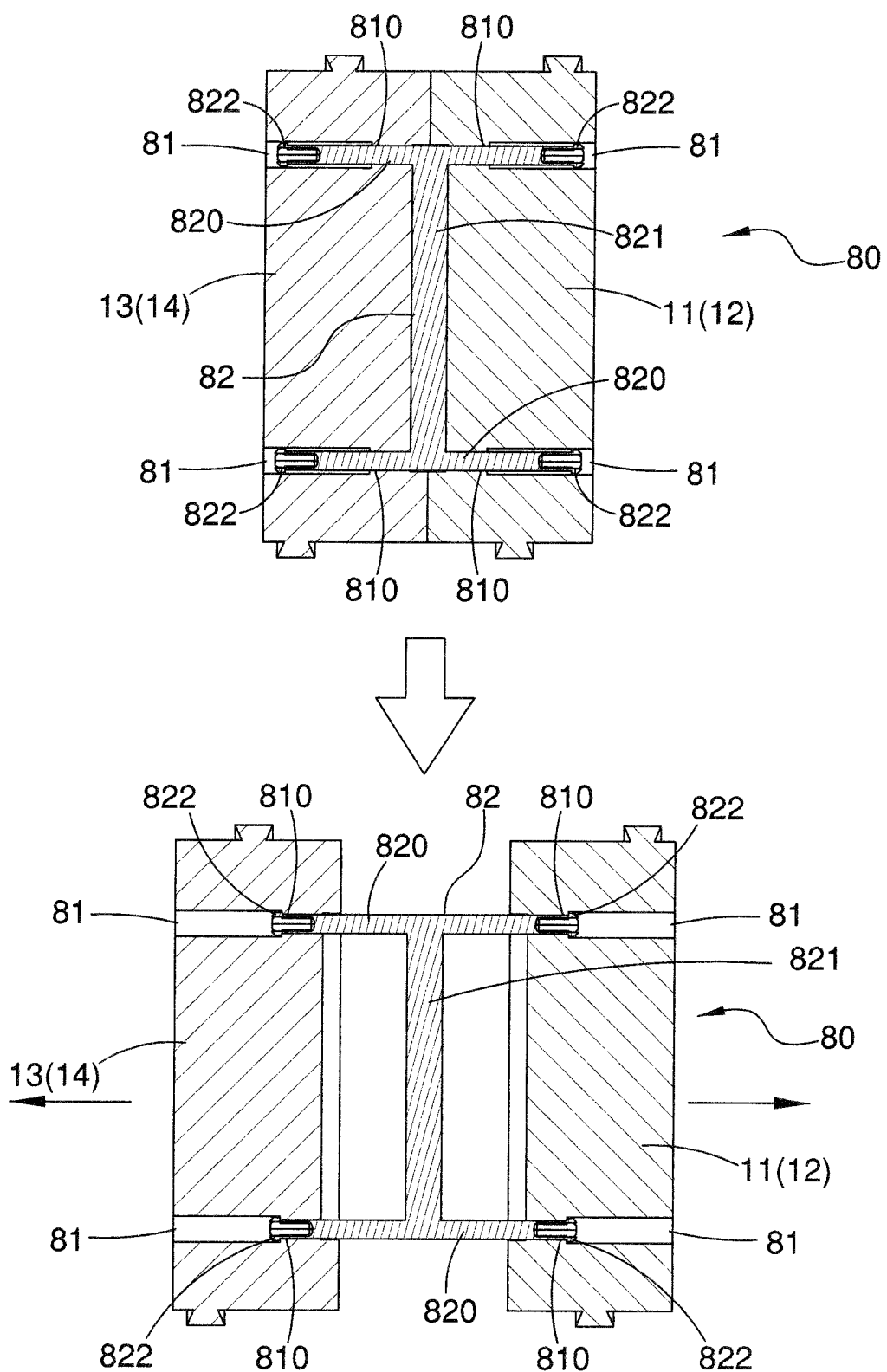
FIG. 22 is a schematic view showing the operation of the guide structure in accordance with the second embodiment of the present invention.

(4) In the second embodiment, two guide structures 80 are disposed between the first and third expansion blocks 11, 13 and between the second and fourth expansion blocks 12, 14, respectively. The two guide structures 80 facilitate the first and third expansion blocks 11, 13 and the second and fourth expansion blocks 12, 14 to move synchronously when they are expanded longitudinally. Referring to FIG. 22, the two guide structures 80 include a plurality of guide holes 81 that are transversely formed in the first, second, third and fourth expansion blocks 11, 12, 13, 14 (in this embodiment, two guide holes are taken as an example) and two guide members 82. The inner ends of the plurality of guide holes 81 each have a flange 810 with a smaller inner diameter. The two guide members 82 are disposed between the first and third expansion blocks 11, 13 and between the second and fourth expansion blocks 12, 14, respectively. Each of the guide members 82 includes two parallel guide rods 820 and a connecting rod 821 connected between the central portions of the two guide rods 820. Respective two ends of the two guide rods 820 of the two guide members 82 are telescopically inserted into the plurality of guide holes 81. The two ends of each guide rod 820 have two enlarged heads 822 with larger outer diameters that can be elastically retracted. When the guide rods 820 are inserted in the guide holes 81, the enlarged heads 822 are blocked by the flanges 810 of the guide holes 81 to prevent the guide rods 820 from being easily detached from the guide holes 81. Thus, when expanded laterally, the first and third expansion blocks 11, 13 and the second and fourth expansion blocks 12, 14 can be smoothly moved through the two guide structures 80, respectively. When expanded longitudinally, the first and third expansion blocks 11, 13 and the second and fourth expansion blocks 12, 14 can be synchronously moved up and down through the two guide structures 80, respectively.

Figure 23:
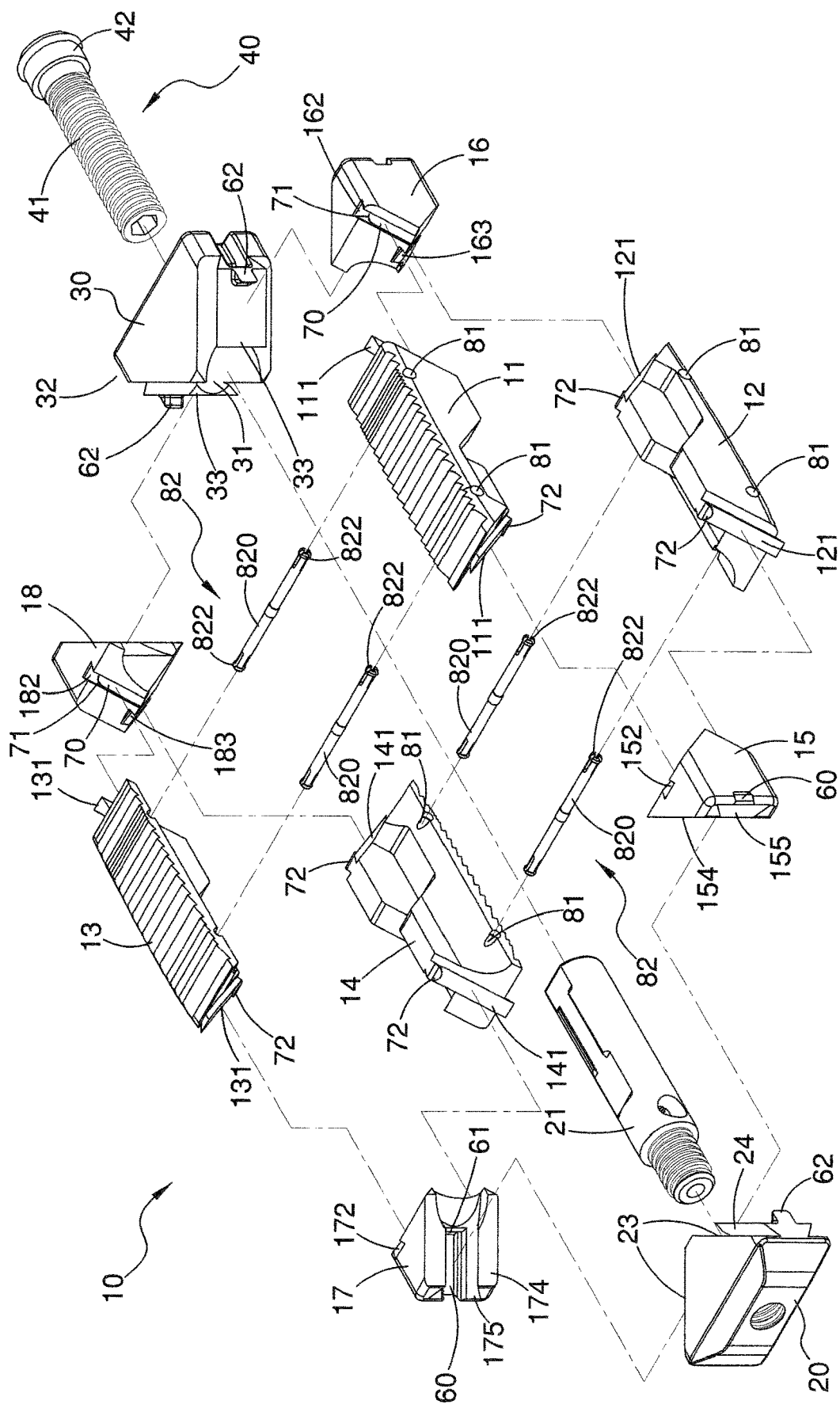
FIG. 23 is an exploded view in accordance with a third embodiment of the present invention.

FIG. 23 illustrates a third embodiment of the multi-section expandable device of the present invention. The third embodiment is substantially similar to the second embodiment with the exceptions described hereinafter. In the third embodiment, the two guide members 82 each include two guide rods 820, without the connecting rod 821. In the third embodiment, the two guide members 82 each may include one, three or more guide rods 820. Because it is only an increase or decrease in number, the details will not be repeated.

Figure 24:
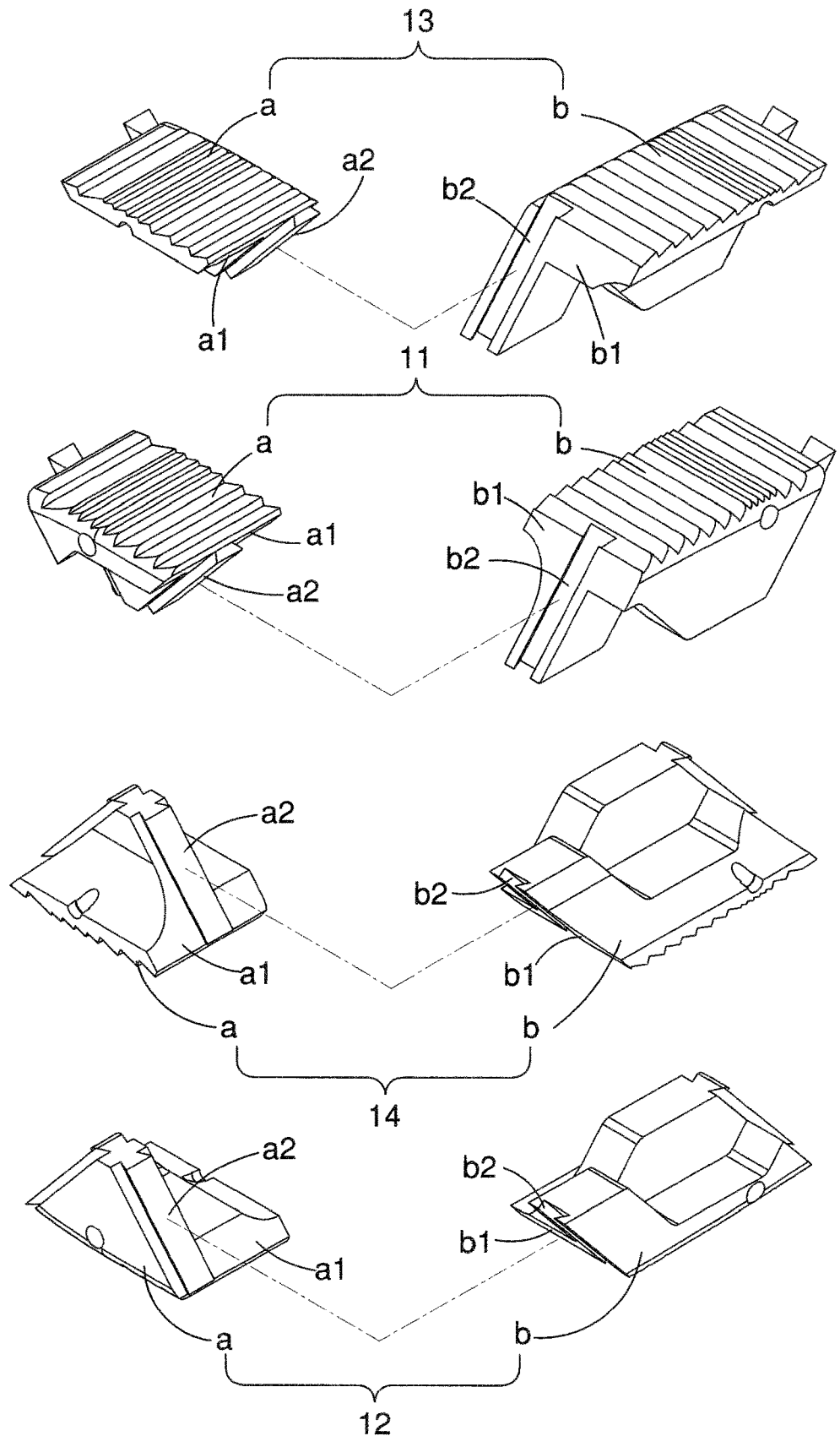
FIG. 24 is a partial enlarged view in accordance with a fourth embodiment of the present invention.
Figure 25:
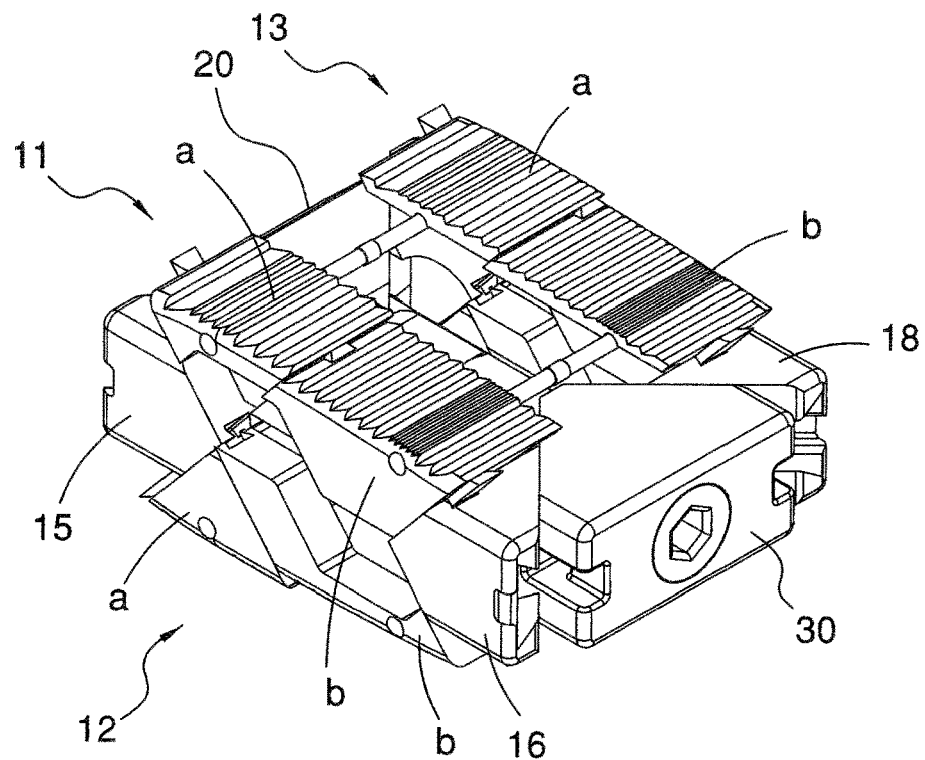
FIG. 25 is a perspective view showing the second-stage longitudinal expansion in accordance with the fourth embodiment of the present invention.
Figure 26:
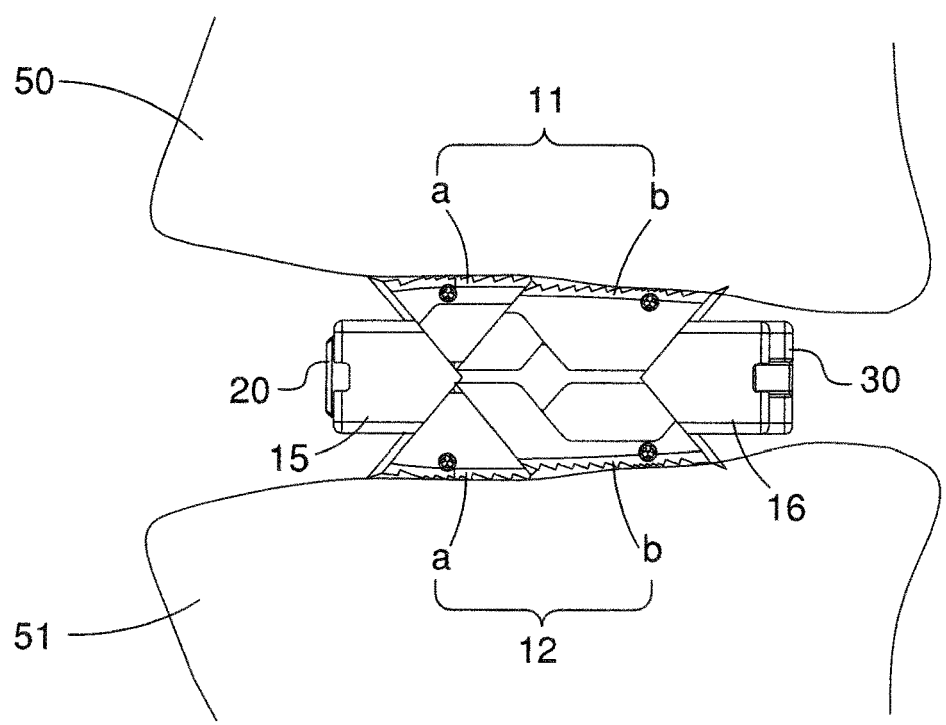
FIG. 26 is a schematic view showing the second-stage longitudinal expansion in accordance with the fourth embodiment of the present invention when in use.

FIGS. 24-26 illustrate a fourth embodiment of the multi-section expandable device of the present invention. The fourth embodiment is substantially similar to the third embodiment with the exceptions described hereinafter. In the fourth embodiment, the first expansion block 11, the second expansion block 12, the third expansion block 13 and the fourth expansion block 14 each comprise a front block a and a rear block b. The front block a and the rear block b are slidably connected to each other with corresponding inclined connecting faces a1, b1. The corresponding inclined connecting faces a1, b1 are provided with a dovetailed groove b2 and a guide rail a2 to be engaged with each other. The plurality of front blocks a and the plurality of rear blocks b can be expanded longitudinally to mate uneven opposite faces of the upper and lower vertebrae 50, 51 to form the second-stage expansion, so that the upper and lower sides of the first expansion block 11, the second expansion block 12, the third expansion block 13 and the fourth expansion block 14 can match the shape, height or angle of the opposite faces of the upper and lower vertebrae 50, 51 to make an adjustment so as to obtain good and stable support, which can be applied to patients with different conditions.

In the present invention, the first upper dovetailed groove 152 and the first inclined plane guide rail 111, the first lower dovetailed groove 153 and the second inclined plane guide rail 121, the second upper dovetailed groove 162 and the first inclined plane guide rail 111, the second lower dovetailed groove 163 and the second inclined plane guide rail 121, the third upper dovetailed groove 172 and the third inclined plane guide rail 131, the third lower dovetailed groove 173 and the fourth inclined plane guide rail 141, the fourth upper dovetailed groove 182 and the third inclined plane guide rail 131, the fourth lower dovetailed groove 183 and the fourth inclined plane guide rail 141, the first and third front dovetailed grooves 155, 175 and the two first push member guide rails 24, the second and fourth rear dovetailed grooves 165, 185 and the two second push member guide rails 33, the dovetailed groove b2 and the guide rail a2 may be other concave and convex engaging structures that can be slidably engaged with each other.

Figure 27:
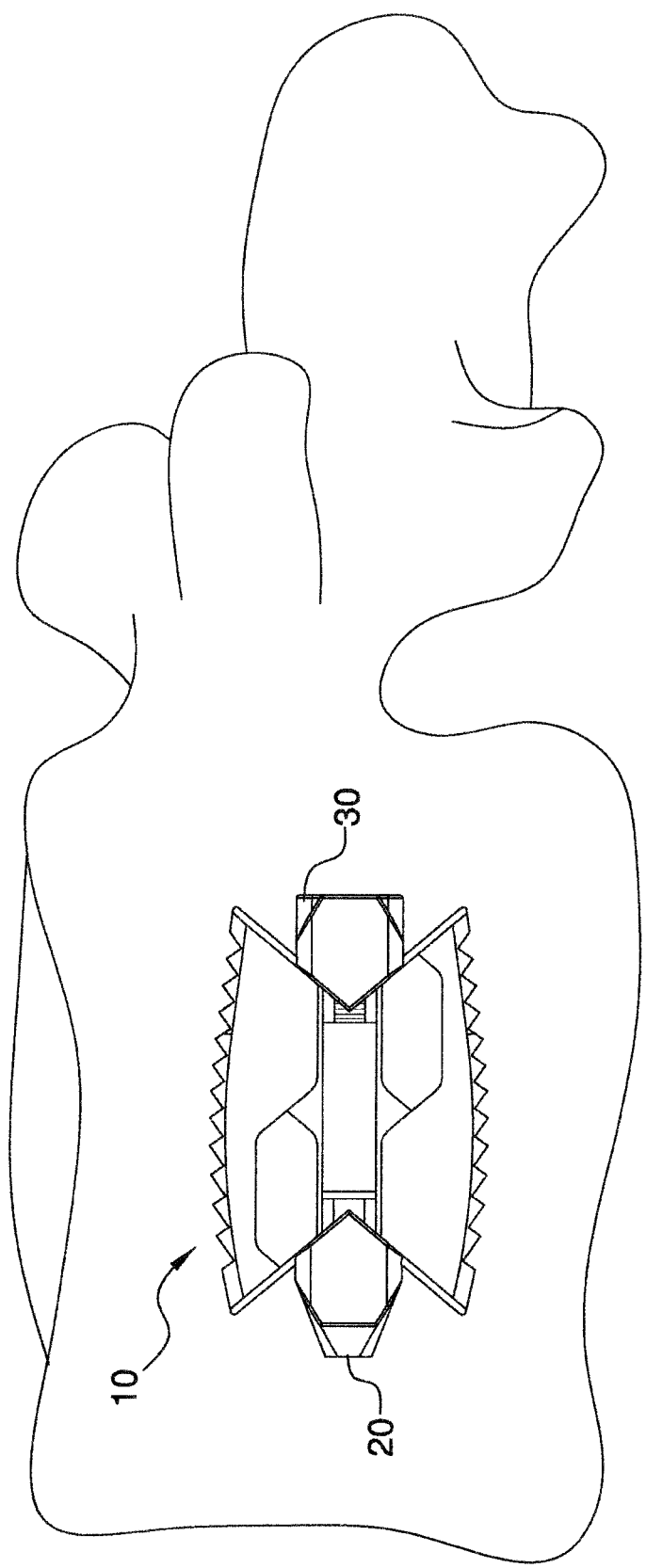
FIG. 27 is a schematic view of the present invention implanted in a bone.

Referring to FIG. 27, the multi-section expandable device of the present invention may be applied to bones (such as, inside the vertebra of the spine) for the restoration or repair of the depressed fracture. The multi-section expandable device of the present invention may also be applied to other related parts such as a space between intervertebral space, bones or soft tissues (such as restoration or repair of face depression). The material of the multi-section expandable device may be changed depending on the location of the application, for example, it may be metal, polymer material, PE, silicone, etc. The multi-section expandable device can be implanted horizontally or vertically to achieve the above-mentioned functions and scope of application.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A multi-section expandable device, comprising:
   an expansion module, able to expand longitudinally and laterally;
   a first push member, disposed at a front end of the expansion module and having a screw hole therein;
   a second push member, disposed at a rear end of the expansion module and having a through hole therein; and
   a bolt, having a screw portion and a head portion, the screw portion being inserted through the through hole of the second push member and screwed in the screw hole of the first push member, the head portion abutting against one side of the second push member opposite to the first push member;

wherein when the bolt is tightened, the first push member and the second push member are pushed to approach each other so as to push the expansion module to generate a first-stage expansion and a second-stage expansion, the first-stage expansion enables the expansion module to expand laterally so as to adjust its width, the second-stage expansion is performed after the expansion module is laterally expanded to have a maximum width, so that the expansion module is longitudinally expanded to adjust its height;
   wherein the expansion module includes a first expansion block, a second expansion block, a third expansion block, a fourth expansion block, a first guide block, a second guide block, a third guide block, and a fourth guide block; the second expansion block is located under the first expansion block, the third expansion block is located beside the first expansion block, the fourth expansion block is located under the third expansion block; the first guide block is slidably disposed on front end faces of the first and second expansion blocks, the second guide block is slidably disposed on rear end faces of the first and second expansion blocks, the first and second expansion blocks are moved up and down between the first and second guide blocks to expand longitudinally; the third guide block is slidably disposed on front end faces of the third and fourth expansion blocks, the fourth guide block is slidably disposed on rear end faces of the third and fourth expansion blocks, the third and fourth expansion blocks are moved up and down between the third and fourth guide blocks to expand longitudinally; the first push member is slidably disposed on front end faces of the first and third guide blocks, the second push member is slidably disposed on rear end faces of the second and fourth guide blocks, the first and second guide blocks and the third and fourth guide blocks respectively drive the first and second expansion blocks and the third and fourth expansion blocks to move left and right between the first and second push members so as to expand laterally.

2. The multi-section expandable device as claimed in claim 1, wherein
   front and rear ends of the first expansion block are formed with two first inclined planes that are inclined outwardly from bottom to top, respectively;
   front and rear ends of the second expansion block are formed with two second inclined planes that are inclined outwardly from top to bottom, respectively;
   front and rear ends of the third expansion block are formed with two third inclined planes that are inclined outwardly from bottom to top, respectively;
   front and rear ends of the fourth expansion block are formed with two fourth inclined planes that are inclined outwardly from top to bottom, respectively;
   a rear end of the first guide block is formed with a first upper inclined plane and a first lower inclined plane corresponding to the first and second inclined planes on the front ends of the first and second expansion blocks, a front end of the first guide block is formed with a first front inclined plane that is inclined outwardly from back to front;
   a front end of the second guide block is formed with a second upper inclined plane and a second lower inclined plane corresponding to the first and second inclined planes on the rear ends of the first and second expansion blocks, a rear end of the second guide block is formed with a second rear inclined plane that is inclined outwardly from front to back;

a rear end of the third guide block is formed with a third upper inclined plane and a third lower inclined plane corresponding to the third and fourth inclined planes on the front ends of the third and fourth expansion blocks, a front end of the third guide block is formed with a third front inclined plane that is inclined outwardly from back to front;

a front end of the fourth guide block is formed with a fourth upper inclined plane and a fourth lower inclined plane corresponding to the third and fourth inclined planes on the rear ends of the third and fourth expansion blocks, a rear end of the fourth guide block is formed with a fourth rear inclined plane that is inclined outwardly from front to back;

two sides of the first push member have two first push member inclined planes corresponding to the first and third front inclined planes;

two sides of the second push member have two second push member inclined planes corresponding to the second and fourth rear inclined planes;

concave and convex engaging structures that can be slidably engaged with each other are disposed between the two first inclined planes and the first and second upper inclined planes, between the two second inclined planes and the first and second lower inclined planes, between the two third inclined planes and the third and fourth upper inclined planes, between the two fourth inclined planes and the third and fourth lower inclined planes, between the two first push member inclined planes and the first and third front inclined planes, and between the two second push member inclined plane and the second and fourth rear inclined planes, respectively.

3. The multi-section expandable device as claimed in claim 2, wherein two first inclined plane guide rails are disposed on the two first inclined planes, respectively; two second inclined plane guide rails are disposed on the two second inclined planes, respectively; two second inclined plane guide rails are disposed on the two second inclined planes, respectively; two fourth inclined plane guide rails are disposed on the two fourth inclined planes, respectively; the first upper inclined plane is provided with a first upper dovetailed groove for the first inclined plane guide rail on the front end of the first expansion block to be inserted therein, the first lower inclined plane is provided with a first lower dovetailed groove for the second inclined plane guide rail on the front end of the second expansion block to be inserted therein, the first front inclined plane is provided with a first front dovetailed groove; the second upper inclined plane is provided with a second upper dovetailed groove for the first inclined plane guide rail on the rear end of the first expansion block to be inserted therein, the second lower inclined plane is provided with a second lower dovetailed groove for the second inclined plane guide rail on the rear end of the second expansion block to be inserted therein, the second rear inclined plane is provided with a second rear dovetailed groove; the third upper inclined plane is provided with a third upper dovetailed groove for the third inclined plane guide rail on the front end of the third expansion block to be inserted therein, the third lower inclined plane is provided with a third lower dovetailed groove for the fourth inclined plane guide rail on the front end of the fourth expansion block to be inserted therein, the third front inclined plane is provided with a third front dovetailed groove; the fourth upper inclined plane is provided with a fourth upper dovetailed groove for the third inclined plane guide rail on the rear end of the third expansion block to be inserted therein, the fourth lower inclined plane is provided with a fourth lower dovetailed groove for the fourth inclined plane guide rail on the rear end of the fourth expansion block to be inserted therein, the fourth front inclined plane is provided with a fourth rear dovetailed groove; the two first push member inclined planes are provided with two first push member guide rails to be inserted in the first and third front dovetailed grooves; and the two second push member inclined planes are provided with two second push member guide rails to be inserted in the second and fourth rear dovetailed grooves.

4. The multi-section expandable device as claimed in claim 3, wherein two first front stop pieces are protruded from a lower end of the first front inclined plane, two second rear stop pieces are protruded from a lower end of the second rear inclined plane, two third front stop pieces are protruded from a lower end of the third front inclined plane, two fourth rear stop pieces are protruded from a lower end of the fourth rear inclined plane; the first push member has two first stop faces on upper and lower sides thereof, the second push member has two second stop faces on upper and lower sides thereof; when the two first stop faces and the two second stop faces are respectively blocked by the two first front stop pieces, the two third front stop pieces and the two second rear stop pieces, the two four rear stop pieces, the first and second expansion blocks and the third and fourth expansion blocks cannot continue to expand laterally, thereby achieving an ultimate width of the first-stage expansion.

5. The multi-section expandable device as claimed in claim 4, wherein each of the first upper dovetailed groove, the first lower dovetailed groove, the second upper dovetailed groove, the second lower dovetailed groove, the third upper dovetailed groove, the third lower dovetailed groove, the fourth upper dovetailed groove and the fourth lower dovetailed groove is provided with a limit guide groove on a bottom thereof, one end of the limit guide groove is an open end, another end of the limit guide groove is formed with an engaging face; one end of each of the two first inclined plane guide rails, the two second inclined plane guide rails, the two third inclined plane guide rails and the two fourth inclined plane guide rails is provided with an engaging portion to be inserted in the limit guide groove; the eight engaging portions are blocked by the engaging faces of the eight limit guide grooves to prevent the first, second, third and fourth expansion blocks from being disengaged from the first, second, third and fourth guide blocks.

6. The multi-section expandable device as claimed in claim 3, wherein each of the first front dovetailed groove, the second rear dovetailed groove, the third front dovetailed groove and the fourth rear dovetailed groove has an ultimate guide groove on a bottom thereof, one end of the ultimate guide groove is an open end, another end of the ultimate guide groove is formed with an ultimate stop face, one end of each of the two first push member guide rails and the two second push member guide rails is provided with a raised portion to be inserted in the ultimate guide groove, when the four raised portions are respectively blocked by the ultimate stop faces of the four ultimate guide grooves, the first and second expansion blocks and the third and fourth expansion blocks cannot continue to expand laterally, thereby achieving an ultimate width of the first-stage expansion.

7. The multi-section expandable device as claimed in claim 6, wherein each of the first upper dovetailed groove, the first lower dovetailed groove, the second upper dovetailed groove, the second lower dovetailed groove, the third upper dovetailed groove, the third lower dovetailed groove, the fourth upper dovetailed groove and the fourth lower dovetailed groove is provided with a limit guide groove on a bottom thereof, one end of the limit guide groove is an open end, another end of the limit guide groove is formed with an engaging face; one end of each of the two first inclined plane guide rails, the two second inclined plane guide rails, the two third inclined plane guide rails and the two fourth inclined plane guide rails is provided with an engaging portion to be inserted in the limit guide groove; the eight engaging portions are blocked by the engaging faces of the eight limit guide grooves to prevent the first, second, third and fourth expansion blocks from being disengaged from the first, second, third and fourth guide blocks.

8. The multi-section expandable device as claimed in claim 1, wherein a rod is protruded from a rear side of the first push member, and the screw hole is disposed in the rod.

9. The multi-section expandable device as claimed in claim 8, wherein one end of the rod is coupled to the first push member in a screwed manner.

10. The multi-section expandable device as claimed in claim 1, wherein a bottom surface of the first expansion block has a plurality of first guide protrusions and a plurality of first guide grooves which are staggered and each have a trapezoidal shape; a top surface of the second expansion block has a plurality of second guide grooves and a plurality of second guide protrusions which can be slid up and down relative to the plurality of first guide protrusions and the plurality of first guide grooves; a bottom surface of the third expansion block has a plurality of third guide protrusions and a plurality of third guide grooves which are staggered and each have a trapezoidal shape; a top surface of the fourth expansion block has a plurality of fourth guide grooves and a plurality of fourth guide protrusions which can be slid up and down relative to the plurality of third guide protrusions and the plurality of third guide grooves.

11. The multi-section expandable device as claimed in claim 1, further comprising two guide structures, the two guide structures being disposed between the first and third expansion blocks and between the second and fourth expansion blocks, respectively; the two guide structures facilitate the first and third expansion blocks and the second and fourth expansion blocks to move synchronously when expanded.

12. The multi-section expandable device as claimed in claim 11, wherein the two guide structures include a plurality of guide holes that are transversely formed in the first, second, third and fourth expansion blocks and two guide members, the two guide members are respectively disposed between the first and third expansion blocks and between the second and fourth expansion blocks, each of the guide members includes at least one guide rod, and two ends of the guide rod are telescopically inserted into corresponding two of the guide holes.

13. The multi-section expandable device as claimed in claim 11, wherein the two guide structures include a plurality of guide holes that are transversely formed in the first, second, third and fourth expansion blocks and two guide members, the two guide members are respectively disposed between the first and third expansion blocks and between the second and fourth expansion blocks, each of the guide members includes two parallel guide rods and a connecting rod connected between central portions of the two guide rods, and respective two ends of the two guide rods are telescopically inserted into the plurality of guide holes.

14. The multi-section expandable device as claimed in claim 1, wherein the first expansion block, the second expansion block, the third expansion block and the fourth expansion block each comprise a front block and a rear block, the front block and the rear block are slidably connected to each other with corresponding inclined connecting faces, the front blocks and the rear blocks of the first, second, third and the fourth expansion blocks can be expanded longitudinally to mate uneven opposite faces of upper and lower vertebrae to form the second-stage expansion.

15. The multi-section expandable device as claimed in claim 14, wherein the corresponding inclined connecting faces are provided with a dovetailed groove and a guide rail to be engaged with each other.

\* \* \* \* \*